(12) United States Patent
Park et al.

(10) Patent No.: US 11,802,862 B2
(45) Date of Patent: Oct. 31, 2023

(54) ELECTRONIC DEVICE AND METHOD FOR DETERMINING KIND AND STATE OF FOOD STORED THEREIN

(71) Applicant: SAMSUNG ELECTRONICS CO., LTD., Suwon-si (KR)

(72) Inventors: Jangpyo Park, Suwon-si (KR); Yongwon Jeong, Suwon-si (KR); Seonghwan Kim, Suwon-si (KR); Heejin Park, Suwon-si (KR); Joonho Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 464 days.

(21) Appl. No.: 17/001,138

(22) Filed: Aug. 24, 2020

(65) Prior Publication Data
US 2021/0055275 A1    Feb. 25, 2021

(30) Foreign Application Priority Data

Aug. 22, 2019    (KR) .................. 10-2019-0103299

(51) Int. Cl.
   *G01N 33/02* (2006.01)
   *G01N 33/00* (2006.01)
   *G01N 21/78* (2006.01)

(52) U.S. Cl.
   CPC ........... *G01N 33/02* (2013.01); *G01N 21/783* (2013.01); *G01N 33/0062* (2013.01)

(58) Field of Classification Search
   CPC .. G01N 33/02; G01N 21/783; G01N 33/0062; G01N 1/2214; G01N 1/2226;
   (Continued)

(56) References Cited

U.S. PATENT DOCUMENTS

| 5,968,766 A | 10/1999 | Powers |
| 2003/0003589 A1 | 1/2003 | Khalil et al. |

(Continued)

FOREIGN PATENT DOCUMENTS

| CN | 209246487 U | 8/2019 |
| EP | 3029456 A1 | 6/2016 |

(Continued)

OTHER PUBLICATIONS

Communication dated Jun. 20, 2022 by the European Patent Office for European Patent Application No. 20855281.0.

(Continued)

*Primary Examiner* — Robert R Raevis
(74) *Attorney, Agent, or Firm* — Sughrue Mion, PLLC

(57) ABSTRACT

The disclosure relates to an electronic device and a method for determining the kind and the state of a food stored therein. The electronic device includes a storage container in which the food is stored, a gas detecting device for detecting a gas included in air in the storage container, and at least one processor that identifies a time point, at which the gases included in the air in the storage container are extracted, on the basis of at least one temperature profile of the gas detecting device, and identifies a time point at which the gases included in the air in the storage container are extracted, on the basis of a configuration of at least one adsorption material included in the gas detecting device.

18 Claims, 13 Drawing Sheets

(58) Field of Classification Search
CPC .......... G01N 33/0011; G01N 33/0044; G01N 33/0054; G01N 33/025; G01N 33/12; F25D 2700/06; F25D 17/042; F25D 29/00; F25D 25/00; F25D 2700/00
USPC .......... 73/19.01, 19.12, 19.02, 23.34, 24.31, 73/863.12, 863.21, 864.81, 865.7
See application file for complete search history.

(56) References Cited

U.S. PATENT DOCUMENTS

| | | |
|---|---|---|
| 2004/0013571 A1 | 1/2004 | Morris |
| 2004/0147038 A1 | 7/2004 | Lewis et al. |
| 2005/0090018 A1 | 4/2005 | Walte et al. |
| 2007/0277589 A1 | 12/2007 | Harden et al. |
| 2011/0005928 A1 | 1/2011 | Manoukian et al. |

FOREIGN PATENT DOCUMENTS

| | | | |
|---|---|---|---|
| EP | 3173772 A1 * | 5/2017 | .......... F25D 17/042 |
| JP | 06-034613 A | 2/1994 | |
| JP | 2013249990 A | 12/2013 | |
| KR | 1020050005900 A | 1/2005 | |
| WO | 2015183090 A1 | 12/2015 | |
| WO | 2018/106082 A1 | 6/2018 | |

OTHER PUBLICATIONS

International Search Report (PCT/ISA/210) and Written Opinion (PCT/ISA/237) dated Nov. 27, 2020 issued by the International Searching Authority in International Application No. PCT/KR2020/011204.

* cited by examiner

ELECTRONIC DEVICE AND METHOD FOR DETERMINING KIND AND STATE OF FOOD STORED THEREIN

CROSS-REFERENCE TO RELATED APPLICATION(S)

This application is based on and claims priority under 35 U.S.C. § 119 to Korean Patent Application No. 10-2019-0103299, filed on Aug. 22, 2019, in the Korean Intellectual Property Office, the disclosure of which is incorporated by reference herein in its entirety.

BACKGROUND

1. Field

The disclosure relates to an electronic device and a method for determining the kind and the state of a food stored therein.

2. Description of Related Art

A general refrigeration system is a device that cools the interiors of a refrigeration chamber and a freezing chamber formed in the interior thereof and freshly stores foods in the refrigeration chamber and the freezing chamber for a long time.

The freshness of the foods stored in the refrigerator may be maintained for a certain period of time, but the foods ripen or eventually decompose over time. A user may monitor the foods by using a memory of the initial storage time point of the foods or by the naked eye, or may determine the ripening degree and the decomposition degree of the foods stored in the refrigerator through recognition, for example, of a scent. However, by these methods, the precision of monitoring the ripening degrees and the decomposition of the foods is low, and the user may forget and frequently miss the expiration date within which the foods can be ingested freshly. Further, the user may be exposed to diseases or illness, such as food poisoning, by ingesting the decomposed foods. Accordingly, a measure for securing safe intake of foods by predicting the ripening and decomposition states of foods has been studied. For example, a measure of predicting the kind and the state of a food by detecting the gases generated from the food has been studied. If a food is decomposed, various kinds of gases, for example, ammonia, hydrogen sulfide, methane, and the like may be generated.

SUMMARY

Provided is an electronic device and a method for detecting a kind and a state of food by measuring gases generated by the food in a storage chamber of the electronic device.

Additional aspects will be set forth in part in the description which follows and, in part, will be apparent from the description, or may be learned by practice of the presented embodiments.

In accordance with an aspect of the disclosure, an electronic device usable for storing foods includes: a storage container; an adsorption member configured to adsorb at least a portion of gas contained in air in the storage container; a heater configured to heat the adsorption member; a gas detecting device including a sensor configured to sense gas desorbed based on the adsorption member being heated; and at least one processor configured to detect at least one of a kind and a concentration of the desorbed gas generated from food stored in the storage container, the at least one processor configured to: control the heater to heat the adsorption member; receive, from the gas detecting device, information on the desorbed gas based on the adsorption member being heated; identify a time point at which the desorbed gas is extracted from the adsorption member based on the received information on the desorbed gas; detect the at least one of the kind and the concentration of the desorbed gas based on at least one of a temperature change of the adsorption member according to the heating of the adsorption member, a predetermined configuration of at least one adsorption material contained in the adsorption member, and the time point at which the desorbed gas is extracted from the adsorption member; and determine a kind and a state of the food based on the detected at least one of the kind and the concentration of the desorbed gas.

The state of the food may include at least one of the state of the food according to a lapsed time after the food is stored, the state of the food according to a freshness or a ripening degree of the food, a cooked state of the food, and a frozen state of the food.

The gas detecting device may be inside the storage container, and the storage container may be a dedicated container for determining the kind and the state of the food.

The gas detecting device may further include: a housing; an opening/closing unit disposed on at least one side of the housing; and a sensor configured to sense the gas desorbed from the adsorption member, and wherein the adsorption member is accommodated in an interior of the housing, and adsorbs the gas contained in the air when the opening/closing unit is opened.

The housing of the gas detecting device may form an at least temporarily closed space according to an operation of the opening/closing unit.

The opening/closing unit may be configured to allow the air in the storage container to flow into the interior of the housing through diffusion.

The gas detecting device may further include a scrubber configured to collect the gas generated from the food.

The electronic device may further include a filter configured to extract a target gas by filtering material desorbed from the adsorption member.

The filter may include a porous material including a metal organic framework (MOF).

A metallic material in the MOF may include at least one of Pt, Zn Cu, Be, Fe, Ni, W, Co, Mn, Mo, Cr, Mg, V, Li, Ca, and Na.

The MOF may include a material having at least one functional group of —COOCu, —COOAg, —HSO4, —COOLi, —SO3H, —OP(=O)OH2, —P(=O)(OH)2, —OH, and —COOH.

The at least one processor may be further configured to control a temperature of the storage container according to the determined kind and the determined state of the food.

In accordance with another aspect of the disclosure, a method for determining at least one of a kind and a state of foods in an electronic device includes: sampling, using a gas detecting device, gas contained in air in a storage container configured to store food; identifying an extraction time point of the sampled gas while extracting the sampled gas toward the outside of the gas detecting device; and detecting at least one of a kind and a concentration of the gas based on at least one of a temperature change of the gas detecting device, a configuration of a gas marking material contained in the gas detecting device, and the extraction time point of the sampled gas.

The sampling may include: adsorbing at least a portion of the gas contained in the air in the storage container to an adsorption member.

The detecting may include: heating the adsorption member; receiving information of gas desorbed from the adsorption member, from the gas detecting device; identifying a time point at which the desorbed gas is extracted based on the received information; and detecting the at least one of the kind and the concentration of the desorbed gas based on at least one of a temperature change of the adsorption member according to the heating of the adsorption member, a predetermined configuration of at least one adsorption material contained in the adsorption member, and the time point at which the desorbed gas is extracted from the adsorption member.

The detecting may further include: determining the kind and the state of the food by comparing the at least one of the kind and the concentration of the gas detected by the gas detecting device and information contained in a database stored in the electronic device or a server outside the electronic device.

The sampling and the detecting are performed according to a command of a user or a preset period.

The method may further include determining the kind and the state of the food according to the detecting and controlling a temperature of the storage container according to the determined kind and the determined state of the food.

The method may further include determining the kind and the state of the food according to the detecting and controlling a humidity of the storage container according to the determined kind and the determined state of the food.

The method may further include determining the kind and the state of the food according to the detecting, wherein the state of the food may include at least one of the state of the food according to a lapsed time after the food is stored, the state of the food according to a freshness or a ripening degree of the food, a cooked state of the food, and a frozen state of the food.

In accordance with another aspect of the disclosure, an electronic device includes: a memory storing instructions; and at least one processor configured to execute the instructions to: control a gas detecting device to heat an adsorption member for adsorbing at least a portion of gas contained in air in a storage container; receive information on gas desorbed based on the adsorption member being heated; identify a time point at which the desorbed gas is extracted from the adsorption member based on the received information on the desorbed gas; detect at least one of a kind and a concentration of the desorbed gas based on at least one of a temperature change of the adsorption member according to the heating of the adsorption member, a predetermined configuration of at least one adsorption material contained in the adsorption member, and the time point at which the desorbed gas is extracted from the adsorption member; and determine a kind and a state of food stored in the storage container based on the detected at least one of the kind and the concentration of the desorbed gas.

The state of the food may include at least one of the state of the food according to a lapsed time after the food is stored, the state of the food according to a freshness or a ripening degree of the food, a cooked state of the food, and a frozen state of the food.

The at least one processor may be further configured to execute the instructions to control an opening/closing unit to allow the air in the storage container to flow into the gas detecting device.

The at least one processor may be further configured to execute the instructions to control a temperature of the storage container according to the determined kind and the determined state of the food.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
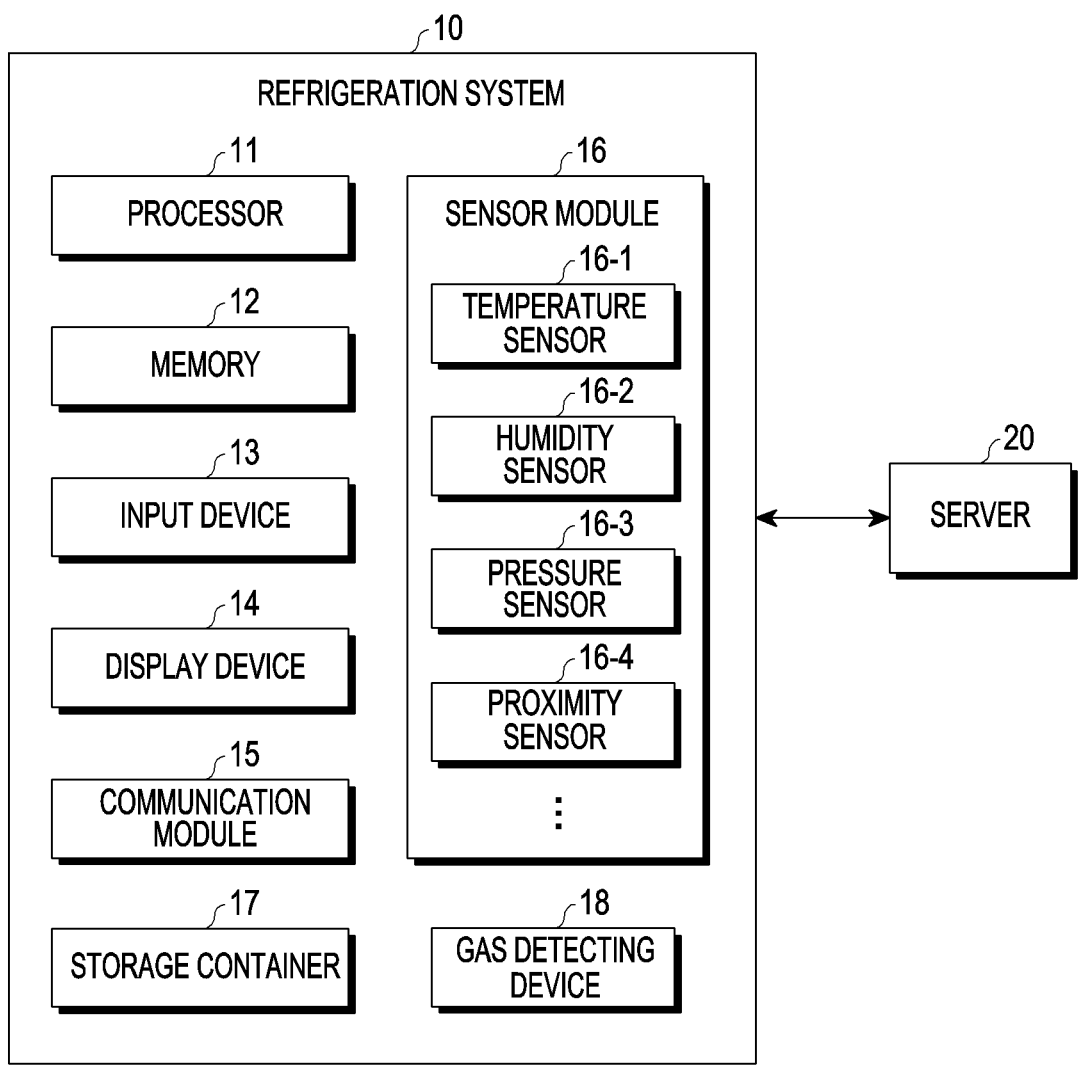
FIG. 1 is a block diagram of an electronic device usable for storing foods according to an embodiment.

Hereinafter, various embodiments of the present disclosure will be described with reference to the accompanying drawings. The same reference numerals denote the same elements in the disclosure.

In the disclosure, reference numerals of operations are used for convenience of description, and the reference numerals do not indicate the sequence of the operations but the operations may be performed in a sequence that is different from the described sequence unless a specific sequence is clearly described in or understood from the context.

FIG. 1 is a block diagram of an electronic device (e.g., a refrigeration system) 10 usable for storing foods according to an embodiment. Referring to FIG. 1, a refrigeration system 10 may include a processor 11 (e.g., at least one processor), a memory 12, an input device 13, a display device 14, a communication module 15, and a sensor module 16.

Although the refrigeration system 10 is described herein as an example of an electronic device, it is understood that the disclosure is not limited thereto. It is noted that one or more embodiments are applicable to any electronic device that is usable for storing foods. For example, an electronic device for storing foods according to another embodiment may not include a separate cooling system. However, in the following description, a refrigeration system will be discussed for convenience of description.

The processor 11, for example, may control at least one element (e.g., a hardware or software element) of the refrigeration system 10 connected to the processor 11 by executing software (e.g., a program), and may perform various data processing or calculations. According to an embodiment, as at least a part of data processing or calculations, the processor 11 may load a command or data received from another element (e.g., the sensor module 15 or the communication module 15) in a volatile memory, may process a command or data stored in the volatile memory, and may store result data in a nonvolatile memory. Further, according to an embodiment, the processor 11 may control an overall operation of the refrigeration system 10. For example, the overall operation may include various operations including a cooling cycle, a defrosting cycle, or a cooling/defrosting cycle that performs both a cooling cycle and a defrosting cycle. The processor 11 may generate a control signal on a configuration of at least one actuator that is operated in a cooling cycle, a defrosting cycle, and/or a cooling/defrosting cycle according to a program and/or data stored in the memory 12.

The memory 12 may store various data used by at least one element (e.g., the processor 11 or the sensor module 15) of the refrigeration system 10. The data, for example, may include software (e.g., a program), and input data or output data for a related command. The memory 12 may include at least one of a volatile or nonvolatile memory. The program may be stored in the memory 12 as software, and for example, may include an operating system, middleware, or an application.

The input device 13 may receive a command or data, which will be used in an element (e.g., the processor 11) of the refrigeration system 10, from the outside (e.g., the user) of the refrigeration system 10. For example, the input device 13 may receive information on the kind of foods stored in the refrigeration system 10. Further, as an example, the input device 13 may receive a target temperature for an internal temperature that is maintained in a storage chamber of the refrigeration system 10. According to various embodiments, the input device 13 may include at least one hardware device such as various buttons, a switch, a pedal, a keyboard, a mouse, various levers, a handle, or a stick for input by the user. In addition, the input device 13 may include a graphical user interface (GUI), such as a touch pad for input by the user. The touch pad may be implemented by a touch screen panel (TSP) and may have a structure in which the display device 14 and a plurality of layers are laminated.

The display device 14 may visually provide information to the outside (e.g., the user) of the refrigeration system 10. The display device 14, for example, may correspond to a device, such as a display, a hologram device, or a projector, and may include a control circuit for controlling the corresponding device. According to an embodiment, the display device 14 may include a touch circuit configured to detect a touch of the input device 13, or a sensor circuit (e.g., a pressure sensor) configured to measure the intensity of a force generated by the touch.

The communication module 15 (e.g., communication interface, communication circuitry, communication device, communicator, etc.) may communicate with an external device (e.g., a server 20 or another electronic device) of the refrigeration system 10 about an operational state (e.g., electric power or a temperature) of the refrigeration system 10 or the information of the foods stored in the refrigeration system 10. A portion of data processing or all o the data processing may be performed by an external device by transmitting various data to the external device by using the communication module 15. The communication module 15 may be configured to transmit and receive data by using any suitable network (e.g., a LAN or an internet) or any suitable communication protocol (e.g., Bluetooth, Wi-Fi, near-field communication (NFC), IEEE 802.15.4, or IEEE 802.11). The information transmitted through the communication module 15 may be in the form of an electronic signal, an electromagnetic signal, an optical signal, or other signals that may be received by a communication module through a communication link that carries a signal, and may be implemented by using an electric wire or cable, an optical fiber, a phone wire, a mobile phone link, a wireless frequency (RF) link, and/or other communication channels.

The sensor module 16 may detect an operation state (e.g., power or a temperature) of the refrigeration system 10 or a state (e.g., the user state) of an external environment, and may generate an electric signal or a data value corresponding to the detected state. According to an embodiment, the sensor module 16, for example, may include a temperature sensor 16-1, a humidity sensor 16-2, a pressure sensor 16-3, and a proximity sensor 16-4. In addition, the sensor module 16 may further include a gesture sensor, an atmospheric pressure sensor, a magnetic sensor, an acceleration sensor, a color sensor, an infrared (IR) sensor, a biometric sensor, or an illumination system.

According to various embodiments, the refrigeration system 10 may further include a storage container 17 and a gas detecting device 18, in addition to the above-described components.

According to an embodiment, the storage container 17 may be a common storage container 17 provided in the refrigeration system 10. According to another embodiment, the storage container 17 may be a specific storage container 17 (hereinafter, a "dedicated container") that is provided at a specific location of the refrigeration system 10 to perform a specific function (e.g., a gas detecting function). According to various embodiments, a plurality of storage containers 17 may be provided in the refrigeration system 10, and one or more storage containers 17 may be specified as dedicated containers to be used.

According to an embodiment, the gas detecting device 18 may be a configuration for detecting at least a portion of the gas generated in the foods stored in the storage container 17. The gas detecting device 18 may be provided in the refrigeration system 10 separately from the sensor module 16. According to various embodiments, the gas detecting device 18 may be disposed on an outside of the storage container 17 but close to the storage container 17 or may be provided in an interior space of the storage container 17. When a plurality of storage containers 17 are provided, a plurality of gas detecting devices 18 may be provided for the plurality of storage containers 17, respectively in a 1:1 relationship or in a 1:many relationship, or the gas detecting device(s) 18 may be allocated to detect only the gas generated in the foods stored in the dedicated container or some of the containers of the refrigeration system 10.

According to various embodiments, the refrigeration system 10 may, additionally or alternatively, further include other elements, in addition to the above-described components. For example, the refrigeration system 10 may further include at least one of an interface, a connector, an antenna module, and a power management module (e.g., a PMIC).

Figure 2:
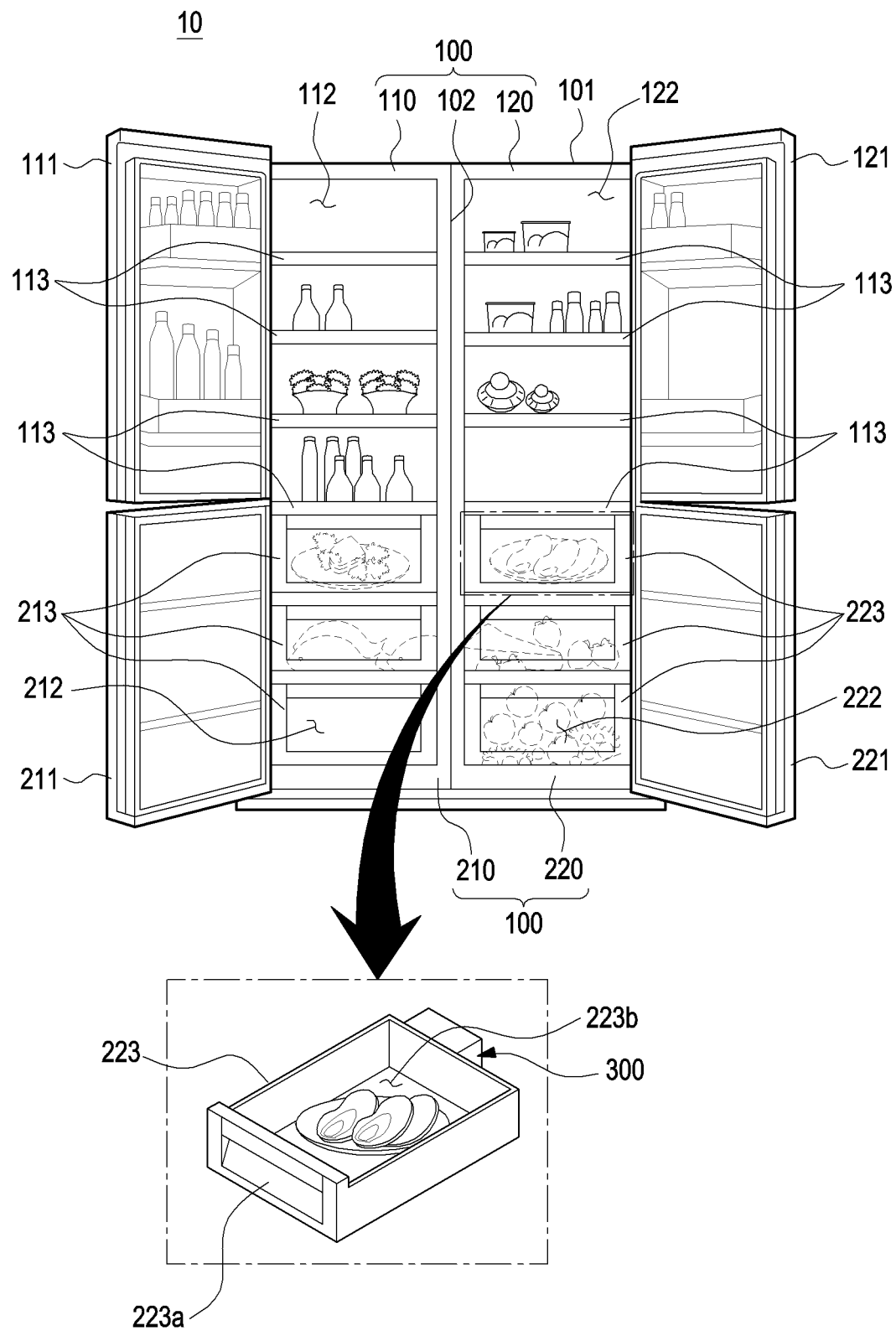
FIG. 2 is a view illustrating a refrigeration system including a gas detecting device according to an embodiment.

FIG. 2 is a view illustrating a refrigeration system 10 including a gas detecting device 300 (e.g., the gas detecting device 18 of FIG. 1), according to an embodiment.

As shown in FIG. 2, the refrigeration system 10 may include a refrigerator 100 that maintains a space for accommodating foods at a specific low temperature or a heating cabinet that maintains the space at a specific high temperature. According to an embodiment, the refrigerator 100 may include a freezing compartment that maintains the space at a specific low temperature below a freezing point. Hereinafter, a refrigerator 100 may be exemplified as the refrigeration system 10.

According to various embodiments, the kind of the refrigerator 100 may be classified according to the forms of the storage chamber and the door. The refrigerator 100 may include a top mounted freezer (TMF) type refrigerator in which a storage chamber is divided into upper and lower sides by a horizontal partition wall such that a freezing compartment is disposed on the upper side and a refrigeration chamber is disposed on the lower side, and a bottom mounted freezer (BMF) type refrigerator in which a refrigeration chamber is disposed on the upper side and a freezing chamber is disposed on the lower side. Further, there may be a side by side (SBS) type refrigerator in which a storage chamber is divided into left and right sides by a vertical partition wall such that a freezing chamber is disposed on one side and a refrigeration chamber is disposed on an opposite side, and there may be a French door refrigerator (FDR) type refrigerator in which a storage chamber is divided into upper and lower sides by a horizontal partition wall such that a refrigeration chamber is disposed on the upper side and a freezing chamber is disposed on the lower side so that the upper refrigeration chamber is opened and closed by a pair of doors. In addition, various embodiments are applicable to any type of refrigerator.

The refrigerator 100 may include a body 101 that defines the external appearance thereof, at least one storage chamber 112, 122, 212, and 222 provided in the interior of the body 101 such that the front surface thereof is opened, and at least one door 111, 121, 211, and 221 coupled to the body 101 to be rotatable to open and close the opened front surface of the storage chamber 112, 122, 212, and 222.

According to an embodiment, the body 101 may include outer walls 110, 120, 210, 220, and partition walls 102 that divide the storage chamber 112, 122, 212, and 222 into a plurality of storage chambers. For example, the storage chambers 112, 122, 212, and 222 may be classified into left/right sides and/or upper/lower sides by the partition walls 102. FIG. 2 illustrates that the storage chambers 112, 122, 212, and 222 are classified into left/right sides by the partition walls 102, although it is understood that one or more other embodiments are not limited thereto.

The storage chambers 112, 122, 212, and 222 may be provided with a plurality of shelves 113 and/or storage containers 223 such that foods may be positioned or accommodated thereon or therein. The shelves 113 and/or storage containers 223 may be configured such that the partition wall 102 may divide the storage chambers 112, 122, 212, and 222, and additionally or alternatively, may divide the storage chambers 112, 122, 212, and 222 in more detail.

The refrigerator 100 may be provided with a cooling system (e.g., the cooling system 150 of FIG. 5, which is described below) to maintain the refrigerator 100 in a low temperature state. The cooling system 150 may be provided in the interior of the body 101 of the refrigerator 100, and may be disposed in a space that is different from the storage chambers 112, 122, 212, and 222 in which the foods are stored. The cooling system 150 may include various configurations and components for circulating cold air, for example, a passage (e.g., a passage 151 of FIG. 5, which is described below), a compressor, a condenser, an expansion valve, an evaporator, a heat exchanger, a blowing fan, and a cold air duct.

In FIG. 2, the shelves 113 and/or the storage containers 223 provided in the refrigerator 100 may be configurations corresponding to the container 17 illustrated in FIG. 1. Accordingly, from the purpose as described in FIG. 1, the gas detecting device 300 (e.g., the gas detecting device 18 of FIG. 1) for detecting gas may be provided close to the shelves 113 and/or the storage containers 223 provided in the refrigerator 100. Gases generated in various foods provided in the shelves 113 and/or the storage containers 223 may be detected by using the gas detecting device 300. For example, the gas detecting device 300 may detect various kinds of gases, such as ethylene, ammonia, methyl mercaptan, hydrogen sulfide, acetic acid, methyl amine, trimethyl amine (TMA) or dimethyl sulfide while classifying them. For reference, ethylene, by way of example, may be a gas generated when fruits and vegetables are ripened and decomposed, and ammonia and methyl mercaptan may be gases generated when meat is ripened and decomposed. The fruits may generate different kinds of gases in addition to ethylene according to the kind of fruit. The gas detecting device 300 according to an embodiment may detect various kinds of gases generated in foods and may utilize (or another processor or computing device may utilize) the detected gases as information for determining the kinds of the foods. Further, according to an embodiment, the gas detecting device 300 may detect a gas of a low concentration of several ten ppm or less as well as gas of a concentration of several hundreds of ppm or more generated in the process of the foods ripening and decomposing. That is, according to various embodiments, not only the kind of the gas but also the concentration of the gas may be detected by using the gas detecting device 300.

The gas detecting device 300 may be mounted in the interiors of the shelves 113 and/or the storage containers 223 or on the outside of the shelves 113 and/or the storage containers 223 (or a combination thereof). Referring to FIG. 2, for example, the gas detecting device 300 may be provided outside the storage container 223. Hereinbelow, among various food storing spaces (the shelves 113 and/or the storage containers 223), the storage container 223 may be described as an example for convenience of description.

In the embodiment illustrated in FIG. 2, the gas detecting device 300 is attached to the storage container 223 and therefore is extracted or moved together with an extracting or moving of the storage container 223. It is understood, however, that one or more other embodiments are not limited thereto. For example, according to another embodiment, the gas detecting device 300 is fixed to one side of the refrigeration system 10 when the shelves 113 and/or the storage containers 223 are extracted or pulled out.

According to an embodiment, the storage container 223 provided with the gas detecting device 300 may at least temporarily define the outside of the refrigerator 100, other adjacent shelves 113, and/or a space in which the flows of air from the storage containers 223 are interrupted (or closed). Referring to FIG. 2, for example, the storage container 223 may be extracted or inserted from the storage chambers 112, 122, 212, and 222 of the refrigerator 100 toward the outside of a handle 223a or the interior space 223b of the storage container 223 may maintain a closed state when the storage container 223 is completely inserted. The gas that penetrates from the outside of the storage container 223 may be interrupted by maintaining the interior space 223b of the storage container 223 in a closed state, and accordingly, the gas detecting device 300 may detect the gas generated from the foods stored in the storage container 223 more accurately. According to another embodiment, the gas detecting device 300 may define a closed space by itself. This is discussed in detail below with reference to FIG. 5.

Figure 3:
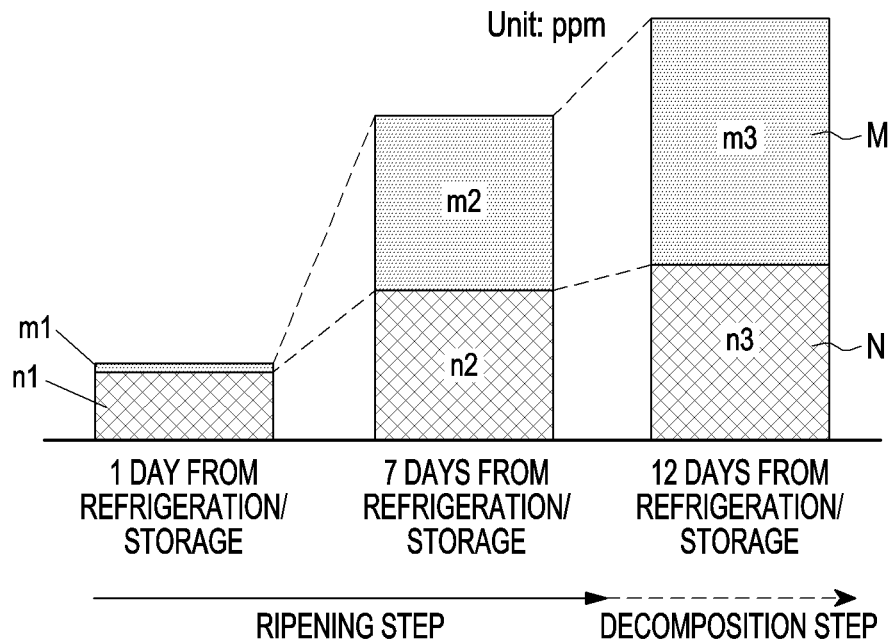
FIG. 3 is a graph depicting ripening/decomposition indexes for ripening degrees of meat according to an embodiment.
Figure 4:
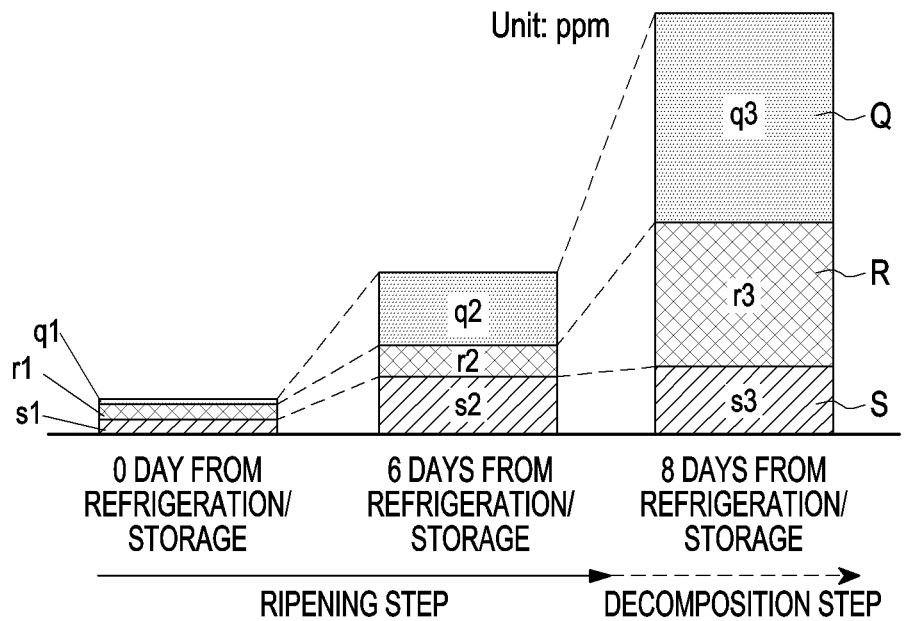
FIG. 4 is a graph depicting ripening/decomposition indexes for ripening degrees of fruits and vegetables according to an embodiment.

FIG. 3 is a graph depicting ripening/decomposition indexes for ripening degrees of fruits according to an embodiment. FIG. 4 is a graph depicting ripening/decomposition indexes for ripening degrees of meat according to an embodiment.

Referring again to FIG. 2, various foods may be stored in the storage chambers 112, 122, 212, and 222 of the refrigerator 100. The kinds of the foods are not limited to a certain specific embodiment. For example, the kinds of the foods may include meat, fish, fruits, and vegetables, and the kinds of meat may include chicken, pork, beef, and lamb. In addition, various kinds of foods may be included.

When the foods are ripened or decomposed, various kinds of gases are generated. Among the generated gases, the gases closely related to the ripening degree of the foods include ammonia and ethylene, and the concentration of the gases increases in proportion to the ripening degree of the foods because the foods are ripened while the gases are not detected in a fresh state.

For reference, the "ripening" here refers to fermentation or excellent ripening by operations of enzymes or microorganisms. The "decomposition" refers to a phenomenon in which organisms are decomposed while generating bad smells through operations of microorganisms, and occurs when a considerable period of time elapses in the ripening step. If the foods kept in the refrigerator 100 are kept for a long time, the foods are decomposed after the ripening step, and bad smells may be generated in the refrigerator 100 due to the decomposed foods and the health of the user may be damaged if the decomposed foods are ingested.

Moreover, the components and the concentrations of the gases may differ greatly according to the kinds of the foods and the time for ripening. In a certain food, gases of a high concentration of several hundred ppm or more are generated during the same ripening period of time, and in another food, gases of a low concentration of as low as a maximum of several tens of ppm may be generated during the same ripening period of time.

For example, referring to FIG. 3, in the fruits, various gases may be generated as the fruits are ripened, and the gases generally include ethylene (M), and may include one or more kinds of volatile organic compounds (VOCs) (N). For example, the fruits (apples) may include 39 kinds of VOCs. In the fruits (e.g., apples), ethylene (M), the amount of which is relatively fine (n1) as compared to a predetermined amount (m1) of VOCs (N), is detected from the initial refrigeration storage day to about one day after the fruits are refrigerated and stored. Further, from about 7 days from the refrigeration storage, ethylene (M) is discharged (for example, m2>n2 in the seventh day, m3>n3 in the twelfth day) to have a concentration that is higher than the concentration of the VOCs (N), and it may be identified from a comparison with the detection of the first day that ethylene is detected to have a concentration that is several tens of times as thick as that of the first day. The detailed value for the concentration may vary according to various kinds of the fruits, but the distribution of the gases generated when the fruits are ripened may be as shown in FIG. 3. That is, in the fruits, ethylene may be utilized as an index gas for the ripening degree, as ethylene is a gas that directly causes decomposition of fruits or vegetables.

By way of another example, in the meat (beef), various gases may be generated as the meat is ripened, and the gases may include ammonia (Q) and sulfuric compounds (R), and may include one or more kinds of volatile organic compounds (VOCs) (S). However, referring to FIG. 4, it can be identified that ammonia (Q) is not generated or is hardly generated (q1≈0) from the initial refrigeration storage day to about the 5th day from the refrigeration storage in the meat (beef). Then, a fine amount (r1) of sulfuric compounds (R) and a fine amount (s1) of VOCs (S) may be detected, and may have a concentration (e.g., less than 0.05 ppm) that is difficult to recognize by the sense of smell of the user. Further, it can be identified that even from the refrigeration storage day to about the 6th day after the refrigeration storage, gases (ammonia (q2), sulfuric compounds (r2), and VOCs (s2)) of a concentration of sub ppm (e.g., less than 1 ppm) that cannot be recognized by the sense of smell of the user are generated. Further, in about the 8th day from the refrigeration storage, gases (ammonia (q3), sulfuric compounds (r3), and VOCs (s3)) (e.g., ammonia of 5 ppm or more may be generated in the eighth day) of a concentration that may be recognized by the sense of smell of the user are generated. However, in about the 8th day from the refrigeration storage, the foods may already reach a decomposed step, and may do harm to the health of the user when ingested.

As described above, the kinds of the gases generated may vary according to the kinds of the foods and the ripening degrees of the foods, and the concentrations thereof may vary. The differences may be caused according to the kinds of the foods themselves, but the kinds and the concentrations of the gases detected by several other factors may differ even in the case of the same food. For example, the kinds and the concentrations may be influenced by seasonings added to the foods and additional materials as well as the ripening degrees of the foods themselves, and may be influenced by the method (e.g., may be wrapped to be stored) for storing foods or the closing degrees of the containers.

In this situation, a related art sensor that may generally detect only a gas of a concentration of 5 ppm or more cannot allow the user to properly and promptly receive information on the states of the foods of various kinds stored in the refrigerator According to various embodiments, a gas detecting device 300 that can recognize presence of a low-concentration gas as well as a high-concentration gas and determine the kinds and the states of the foods stored in the refrigerator 100 accurately and promptly is provided.

For reference, the kinds of the foods that may be accommodated in the storage container in the refrigerator are not limited to a certain specific embodiment. Further, the foods, the kinds and the states of which can be determined through the gas detecting device 300, are not limited to a certain specific embodiment.

According to the embodiment illustrated in FIG. 3, ethylene corresponds to the index gas for the ripening degree of fruits (apples), and this may be a target gas that will be detected through the gas detecting device 300. Furthermore, according to the embodiment illustrated in FIG. 4, ammonia corresponds to the index gas for the ripening degree of meat (beef), and this may be a target gas that will be detected through the gas detecting device 300. In this way, according to the kinds of the foods, the target gas to be detected by the gas detecting device 300 may vary or be changed. According to actual experimental results, if a gas generated from the foods in the storage container 223 is detected through the gas detecting device 300, for example, when the fruits have been refrigerated and stored for 7 days, ethylene is detected first. As another example, when meat has been refrigerated and stored for 6 days, ammonia is detected first.

In some embodiments, a plurality of foods may be stored together in the storage container 223 of the refrigerator 100, and index gases of different ripening degrees may be generated by the plurality of foods. In order to provide a more practical method for determining the kind and the state of foods to a user, the gas detecting device 300 may independently detect the target gas even when a plurality of foods are present in one space. That is, even though fruits and meat are stored together in one storage container 223, the gas detecting device 300 can determine the kind and the state of the foods because the kinds of the gases generated according to the ripening degrees of the foods are different.

The gas detecting device 300 according to one or more embodiments is described below in more detail with reference to FIGS. 5 to 9.

In the following description, a "storage container 223" may be described as an example of the storage container. Because the "storage container 223" is substantially the same as or similar to the "storage container 223" described above, the description above may be applied to the following embodiments, and the description provided below may be applied to the above-described embodiments.

Figure 5:
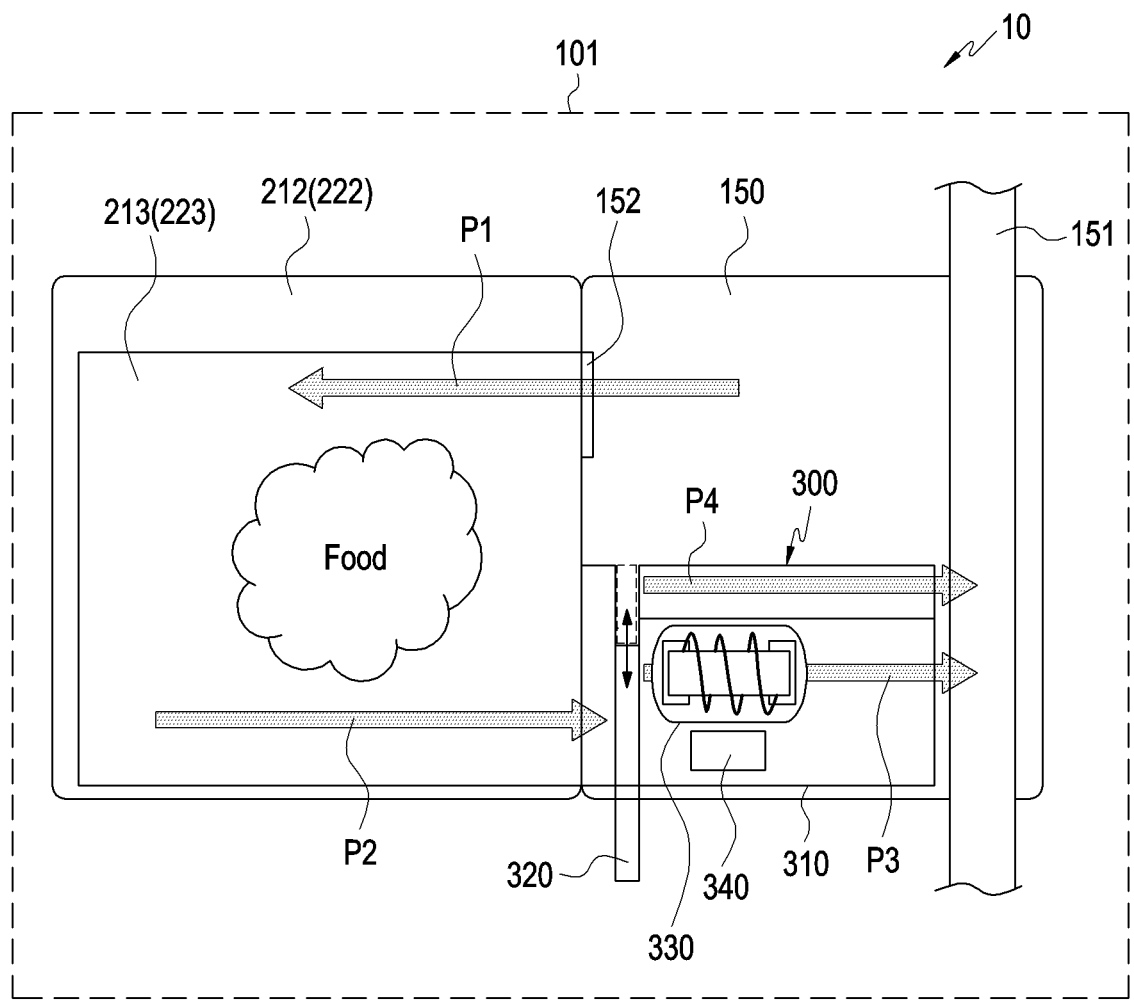
FIG. 5 is a conceptual view of a refrigeration system including a cooling system according to an embodiment.

FIG. 5 is a conceptual view of a refrigeration system 10 including a cooling system 150 according to an embodiment. The embodiment illustrated in FIG. 5 may represent an operation, by the cooling system 150, of providing cold air to the storage container 223 provided in the refrigerator 100 and circulating the cold air.

The cooling system 150 may be a configuration for providing cold air to the storage chambers 112, 122, 212, and 222 divided in the refrigerator 100 and circulating the cold air. The cooling system 150 may be installed on one side of the interior of the body 101 of the refrigerator, and may provide cold air while communicating with the storage chambers 112, 122, 212, and 222 at specific portions. The "cold air" is air of a specific temperature or less, and may exchange heat with a "refrigerant" or coolant in a circulation passage 151 provided in the cooling system 150. According to an embodiment, a separator 152 may be provided on one side of the cooling system 150 to prevent impurities from being included in the cold air P1 that flows toward the storage container 223.

The refrigerator may cause the cold air P1 in the interior of the cooling system 150 to flow toward the storage container 223 by using the cooling system 150. According to an embodiment, the gases in the storage container 223 may be derived of heat to become cold air P2 by the cold air P1 that flows from the cooling system 150 toward the storage container 223. Further, the temperature of the interior of the storage container 223 may be maintained at a specific value through a principle of flowing the cold air P2 to the cooling system 150 again.

According to various embodiments, a gas detecting device 300 may be provided on one side of the storage container 223 of the refrigerator 100, and the cold air P2 in the storage container 223 may be discharged toward the cooling system 150 through the separator 152 or may be discharged toward the cooling system 150 through the gas detecting device 300. According to an embodiment, the gas detecting device 300 may cause the cold air P2 in the storage container 223 to flow toward the cooling system 150 through at least two different passages P3 and P4.

The gas detecting device 300 may include a housing 310, an opening/closing unit 320 provided at least on one side of the housing 310 to open and close the passages P3 and P4, and an adsorption member 330 and a sensor 340 accommodated in the interior of the housing 310.

The housing 310 may have a predetermined size and may be mounted on the interior or the outside of the storage container 223. FIG. 3 illustrates that the housing 310 is mounted on the outside of the storage container 223, although it is understood that one or more other embodiments are not limited thereto. In addition to or in replacement of the embodiment in which the storage container 223 may define a closed space, the housing 310 of the gas detecting device 300 may also define a closed space. If the housing 310 defines a closed space, the gases outside the gas detecting device 300 can be prevented from being introduced into the housing 310 as long as there is not a particular situation (e.g., an opening/closing operation of the opening/closing unit 320).

The opening/closing unit 320 may be provided on at least one side of the housing 310 to open and close passages P3 and P4. Any one of the passages P3 and P4 may be selectively opened and closed or, as illustrated in FIG. 3, the passage P4 may always be opened and only the passage P3 may be selectively opened and closed. In addition, various embodiments may be applied to the opening/closing features of the passages P3 and P4. If the cold air P2 is discharged through the passage P4, at least a portion of the gases included in the cold air P2 may be detected by the gas detecting device 300.

The flows of the cold air from the housing 310 toward the adsorption member 330 may be adjusted by using the opening/closing unit 320. As the cold air P2 in the storage container 223 flows toward the adsorption member 330, the ripening degree and the decomposition degree of the foods in the storage container 223 can be detected. The type of the opening/closing unit 320 may vary in various embodiments. For example, as the opening/closing unit 320, a variable shutter or a one-way valve (e.g., a relief valve or a safety valve) may be used. For reference, the embodiment illustrated in FIG. 5 includes a variable shutter as the opening/closing unit 320, and the embodiments illustrated in FIGS. 6 and 7 include a one-way valve as the opening/closing unit 320.

According to an embodiment, an actuator pump (e.g., a pump) included in the refrigerator 100 may be used for the circulation of cold air. For example, a flow rate adjusting valve may be additionally provided when the cold air is circulated by using the actuator (e.g., the pump), and the cold air may be circulated by controlling the flow rate adjusting valve according to various operations (e.g., a cooling cycle, a defrosting cycle, and a cooling/defrosting cycle) of the processor 11.

According to another embodiment, an actuator may not be included or used. For example, cold air may be circulated by using an opening/closing operation of the opening/closing unit 320 and diffusion using a temperature difference between the storage container 223 and the cooling system 150. Because the system for circulating cold air has a relatively simple configuration if an actuator (e.g., a pump) is not used as compared with the case in which an actuator is used, an installation cost can be reduced and the mounting performance of other parts in the refrigerator can be increased.

The adsorption member 330 may be a component or device for adsorbing (and/or concentrating) the gases in the cold air supplied according to the passage opening/closing operation of the opening/closing unit 320. The kind and the combination of the material that constitutes the adsorption member 330 may vary. For example, a certain adsorption member 330 may adsorb a first gas better than a second gas, and another adsorption member 330 may adsorb the second gas better than the first gas.

If the passage of the opening/closing unit 320 is opened, the adsorption member 330 may adsorb the gases. If the passage of the opening/closing unit 320 is closed, the adsorption member 330 does not adsorb the gases any more. After a certain degree of gases are adsorbed to the adsorption member 330, the kind and the concentration of the gases can be detected by desorbing the gases. For example, when the opening/closing unit 320 is opened, the cold air P2 in the storage container 223 passes through the adsorption member 330 and flows toward the cooling system 150. In a process of the cold air P2 passing through the adsorption member 330 and flowing toward the cooling system 150, the gases corresponding to the adsorption member may be adsorbed to the adsorption member 330. When the opening/closing unit 320 is closed, the cold air P2 in the storage container 223 does not pass through the adsorption member 330. The gases adsorbed to the adsorption member 330 in an opening operation of the opening/closing unit 320 may then be extracted (or discharged) toward the cooling system 150 while being desorbed from the adsorption member 330.

The sensor 340 has a configuration that is separate from the sensor module 150 described in FIG. 1, and may measure the concentration of the gases by detecting the gases desorbed from the adsorption member 330. According to an embodiment, the sensor 340 may be disposed at a location that is adjacent to the adsorption member 330. The sensor 340 may be configured to detect a plurality of different gases, respectively. That is, various kinds of gases desorbed from the adsorption member 330 may be detected by using the sensor 340. Further, various concentrations of the gases may be detected by using the sensor 340. Various kinds and various concentrations of the gases detected by the sensor 340 may then be utilized to determine which gas is generated in which food or in which ripening state the gas is generated.

Figure 6:
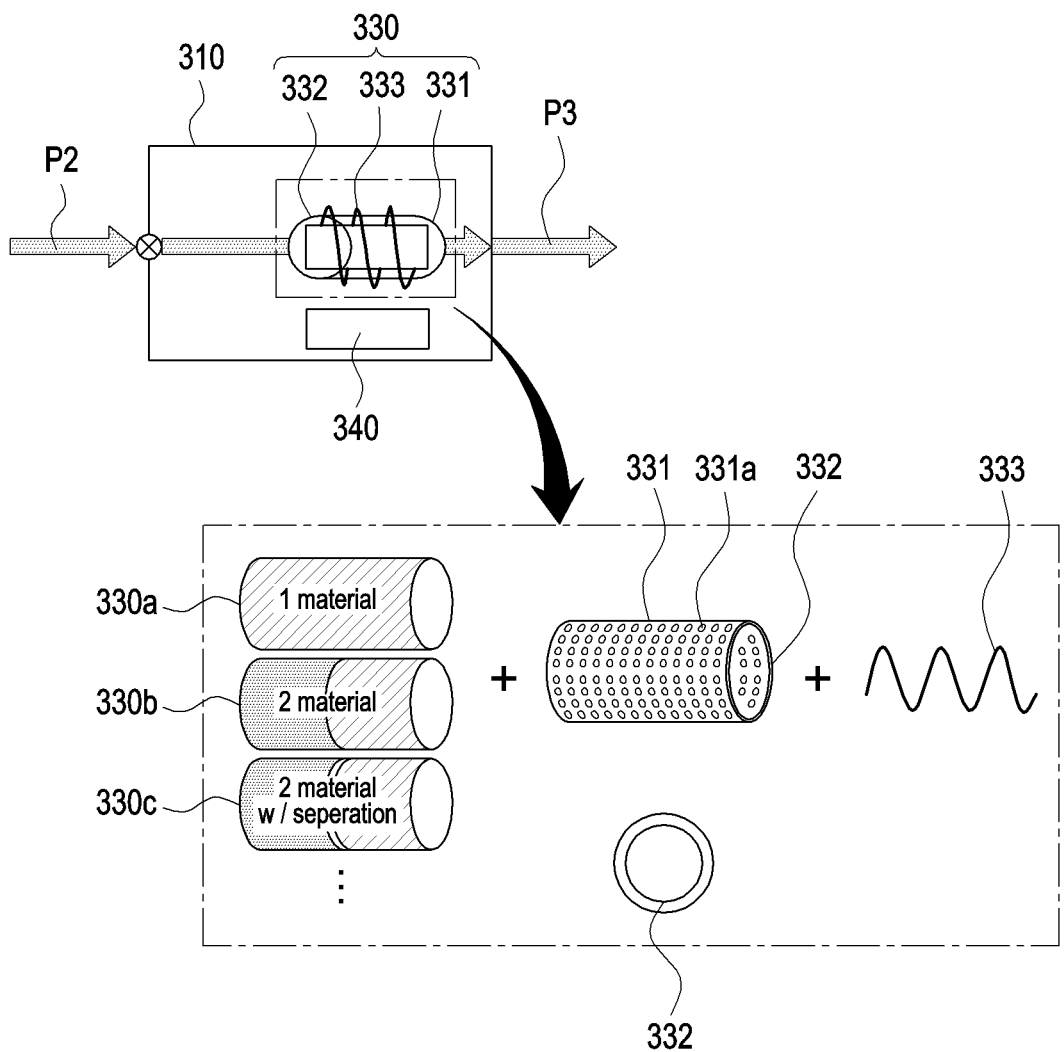
FIG. 6 is a view illustrating a gas detecting device according to an embodiment.

FIG. 6 is a view illustrating a gas detecting device 300 according to an embodiment.

The gas detecting device 300 may include a housing 310, an opening/closing unit 320, an adsorption member 330, and a sensor 340. The adsorption member 330 and the sensor 340 may be disposed in the interior of the housing 310, and the opening/closing unit 320 may be provided on one side of the housing 310 to control the flows of the cold air flowing through the interior of the housing 310.

The adsorption member 330 may adsorb (or concentrate) a target gas from the cold air that circulates in the refrigerator. According to various embodiments, the target gas is a gas related to the freshness (ripening degree) or the decomposition degree of foods, and may include at least one of ethylene, ammonia, methyl mercaptan, a sulfide compound (e.g., hydrogen sulfide), acetic acid, methyl amine, trimethyl amine (TMA) or dimethyl sulfide. It is understood, however, that the target gas is not limited to these specific examples.

The adsorption member 330 may include at least one adsorption member (any one of 330*a*, 330*b*, and 330*c*), a filter unit 331 (e.g., filter), a scrubber 332, and a heating unit 333 (e.g., heater).

The adsorption member 330 may include at least one adsorption material (any one of 330*a*, 330*b*, and 330*c*) that is a configuration or component to which the gases are substantially adsorbed. The configuration of the at least one adsorption material may vary according to various embodiments. For example, the adsorption member 330 may include one kind of adsorption material 330*a*, or two kinds of adsorption materials 330*b*. As another example, when the adsorption member includes two different materials, the percentages of the two different adsorption materials included in the adsorption member may be the same or different. Further, according to an embodiment, the two different adsorption materials included in the adsorption member may be desorbed from each other. Here, when two different adsorption materials are desorbed 330*c*, they may be configured in multi-stages, and a layered structure may be formed between the stages by using a layered structure using individual materials or a separator using glass wool. Further, as an example, two different materials included in the adsorption member may be mixed. In addition, the adsorption member 330 may be configured through combination of three or more adsorption materials.

The at least one adsorption material 330*a*, 330*b*, and 330*c*, for example, may be active carbon, zeolite, sepiolite, or one or more mixtures including the above-described materials. As another example, the at least one adsorption material 330*a*, 330*b*, and 330*c* may include at least one of polydimethylsiloxane or Tenax TA, and may be a complex material in which at least one of porphyrin or phthalocyanine may be coated to improve a selective adsorption performance for the target gas. According to an embodiment, at least one adsorption material 330*a*, 330*b*, and 330*c* may be contained in a small container. The material of the small container may be stainless steel, glass, quartz, or silicon, but is not limited thereto.

The at least one adsorption material 330*a*, 330*b*, and 330*c* may be designated in advance before the refrigeration system 10 is installed. The configuration of at least one adsorption material 330*a*, 330*b*, and 330*b* may be replaced while the refrigeration system 10 is used or after being installed.

The scrubber 332 may be a configuration or component that collects solid or liquid particles that float in the gases in an operation of adsorbing the gases to the adsorption materials 330*a*, 330*b*, and 330*c*. The air contained in the storage container 223 may include gases other than the gases that may be the ripening indexes of the foods. If the other gases are adsorbed into the adsorption materials 330*a*, 330*b*, and 330*c*, they may influence the gas recognition rate of the gas detecting device 300 using the adsorption member 330 as crosstalk. Accordingly, the crosstalk by the other gases may be reduced by using the scrubber 332. According to an embodiment, 90% or more of the gases that cause the crosstalk may be removed by the scrubber 332. According to various embodiments, the scrubber 332 may be formed or provided on one side, an opposite side, or both the sides of the adsorption material 330*a*, 330*b*, and 330*c*.

The heating unit 333 may be a configuration or component for desorbing the gases adsorbed to the adsorption materials 330a, 330b, and 330c if the adsorption materials 330a, 330b, and 330c are heated in a state in which the gases are adsorbed to the adsorption material 330a, 330b, and 330c. The adsorption material 330a, 330b, and 330c may adsorb the gases at a predetermined temperature or less or maintain the adsorption state. If, however, the temperature of the adsorption material 330a, 330b, and 330c exceeds the predetermined temperature, the gases may be eliminated. By increasing the temperature of the adsorption materials 330a, 330b, and 330c to the target temperature within a target period of time by using the heating unit 333, the gases adsorbed to the adsorption materials 330a, 330b, and 330c may be extracted.

The filter unit 331 may be a configuration or component that filters gases other than the target gas desorbed from the adsorption materials 330a, 330b, and 330c by the heating unit 333. The filter unit 331 may include one or more filters, and the filters may have different structures (e.g., a column or a net shape) or may use different filtering components. The filter unit 331 may have a shape in which a plurality of pores are formed on a surface thereof. The filtering components, for example, may include at least one of porous materials, such as Tenax TA, a carbon material, zeolite, an anodized aluminum oxide (AAO), or a metal organic framework (MOF). Further, porphyrin, phthalocyanine, or carbon-based nano materials may be coated on the filtering component. According to various embodiments, the metallic material in the MOF may include at least one of Pt, Zn Cu, Be, Fe, Ni, W, Co, Mn, Mo, Cr, Mg, V, Li, Ca, and Na. According to an embodiment, the MOF may include a material having at least one functional group of —COOCu, —COOAg, —HSO4, —COOLi, —SO3H, —OP(=O)OH2, —P(=O)(OH)2, —OH, and —COOH.

Figure 7:
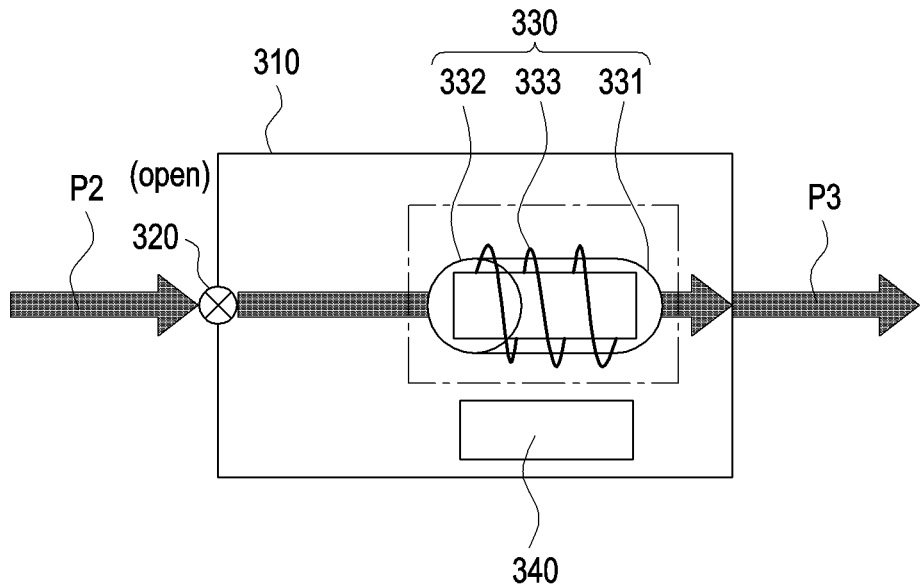
FIG. 7 is a view illustrating a sampling (or adsorption) operation of a gas detecting device according to an embodiment.
Figure 8:
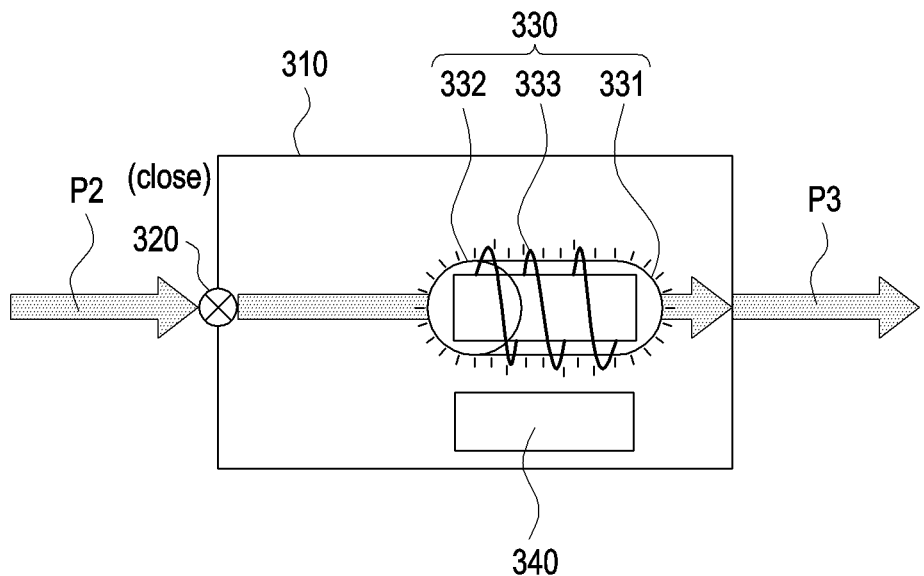
FIG. 8 is a view illustrating a detection (or desorption) operation of a gas detecting device according to an embodiment.

FIG. 7 is a view illustrating a sampling (or adsorption) operation of a gas detecting device 300 according to an embodiment. FIG. 8 is a view illustrating a detection (or desorption) operation of a gas detecting device 300 according to an embodiment.

The gas detecting device 300 may include an adsorption member 330 that adsorbs at least a portion of the gases contained in the air in the storage container 223, and may detect the kinds of the gases by using the gases desorbed from the adsorption member 330.

In order to determine the state of the foods in the storage container 223, first, a portion of the gases contained in the air in the storage container 223 may be sampled.

Referring to FIG. 7, in the sampling (or adsorption) operation of the gas detecting device 300, the opening/closing unit 320 may cause the cold air P2 in the storage container 223 to flow in the housing 310. The cold air P2 that flows in the housing 310 may pass through the adsorption member 330 and flow toward the cooling system 150.

In this process, the gases contained in the cold air may be continuously adsorbed to the adsorption materials 330a, 330b, and 330c in the adsorption member 330. At least a portion of the gases contained in the cold air may be removed by the scrubber 332. Further, a portion of the gases that are not removed by the scrubber 332 may be adsorbed by the adsorption materials 330a, 330b, and 330c. According to an embodiment, the gases contained in the air in the storage container may be exposed to the gas detecting device 300 through diffusion without using a separate actuator. When the diffusion is used, the gas adsorption degrees of the adsorption materials 330a, 330b, and 330c may be generally increased as the state in which the opening/closing unit 320 is opened becomes longer, and through this, a more precise detection result can be acquired.

After a portion of the gases contained in the air in the storage container is sampled, the detection operation of the gas detecting device 300 is performed, and the kind and the state of the foods may be determined by using the obtained information.

Referring to FIG. 8, in the detection (or desorption) operation of the gas detecting device 300, the opening/closing unit 320 may interrupt flows of the cold air P2 in the storage container 223 into the housing 310. If the opening/closing unit 320 does not interrupt the flows of the cold air P2 in the storage container 223 into the housing 310, a new gas may be continuously introduced in the detection operation and may influence the detection result. Accordingly, in a state in which the flows of the cold air are interrupted, that is, in a state in which the interior of the housing 310 is closed, the gas detecting device 300 may desorb the materials adsorbed to the adsorption materials 330a, 330b, and 330c by heating the heating unit 330.

Then, the sensor 340 may measure the concentration of the gases desorbed from the adsorption materials 330a, 330b, and 330c. The sensor 340 may measure the gases desorbed from the adsorption materials 330a, 330b, and 330c in various manners. For example, at least one of a gas chromatography sensor using the adsorption/desorption speed of gases, a mass spectrometry sensor, an enzyme-linked immunosorbant sensor that derives a chemical binding with an enzyme catalyst, a colorimetric sensor that identifies a chemical binding and a reaction through a change in color, an electrochemical sensor that converts a reaction result into an electrical signal such as a PH or a resistance, and a metal oxide sensor (MOS) that identifies a change of electrical conductivity according to a reaction of a surface of a semiconductor and a target gas may be used.

According to an embodiment, before the sensor 340 measures the concentration of the desorbed gases, only a gas that is a measurement target is selected or filtered from among the gases desorbed from the adsorption members 330a, 330b, and 330c through the filter unit 331, and the concentration of the selected gas may be measured.

According to various embodiments, the sequence of the gases desorbed from the adsorption materials 330a, 330b, and 330c according to the specific temperature profile in the process of heating the heating unit 330 may vary or be changed.

According to various embodiments, the sequence of the gases desorbed from the adsorption materials 330a, 330b, and 330c according to the kinds of the adsorption materials 330a, 330b, and 330c included in the adsorption member 330 in the process of heating the heating unit 330 may vary or be changed.

Figure 9A:
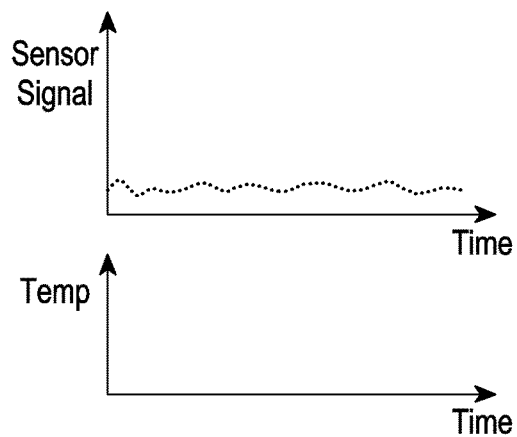
FIGS. 9A to 9C are views illustrating a state in which two different kinds of gases are extracted at different time points on the basis of a temperature change of a gas detecting device.
Figure 9B:
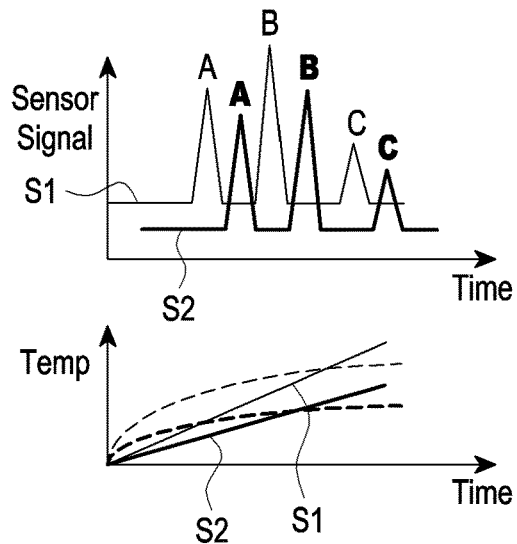
Figure 9C:
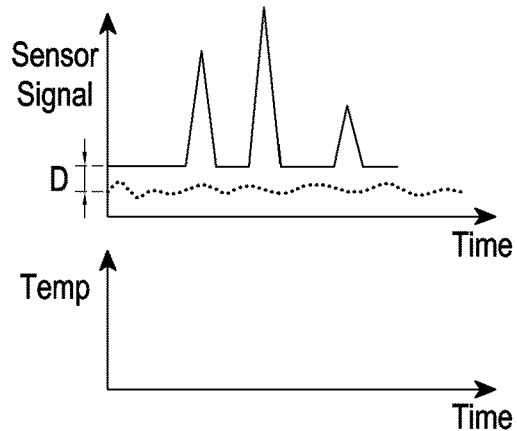

FIGS. 9A to 9C are views illustrating a state in which two different kinds of gases are selected on the basis of the temperature profile of the adsorption member 330.

FIG. 9A is a view illustrating a sensor signal in a sampling operation for the adsorption member 330.

Referring to FIG. 9A, in the sampling operation, the opening/closing unit 320 of the gas detecting device 300 may cause the air in the storage container 223 to flow toward the housing 310. Then, the sensor 340 may measure the concentration of the gases in the surrounding environment by using a baseline signal. Here, the measurement of the surrounding environment may mean measurement of whether there is a target gas and/or other gases around the adsorption member 330. For example, when the operation for detecting a target gas by the gas detecting device 300 is not an initial operation, that is, the detection operation is performed at least once before, there may be present a residual target gas around the adsorption member 330, and this may influence the determination of the current state of the foods in the refrigeration system 10. Further, when there are gases other than the target gas in the storage container 223, they may influence the determination of the state of the foods in the refrigeration system 10. Accordingly, the baseline data according to a baseline signal may be secured in advance by using the sensor unit 340 to minimize the influence, and through this, a more precise result may be derived.

FIG. 9B is a view illustrating a sensor signal in a detecting operation for the adsorption member 330.

In the detection mode, the opening/closing unit 320 of the gas detecting device 300 is closed, and the interior of the housing 310 may be in a closed state. Further, the heating unit 340 may heat the adsorption member 330, and may desorb the gases (concentrated materials) adsorbed to the at least one adsorption material 330a, 330b, and 330c.

The kinds and the combinations of the adsorption materials 330a, 330b, and 330c may vary. The kind and the concentration of the adsorbed gas may also vary according to the variety of the kinds and the combinations of the adsorption materials 330a, 330b, and 330c. Accordingly, the kinds and the concentrations of the gases desorbed from the adsorption materials 330a, 330b, and 330c when the adsorption materials 330a, 330b, and 330c are heated may vary. Like the variety of the kinds and the combinations of the adsorption materials 330a, 330b, and 330c, temperatures (temperature profiles) for desorbing a certain gas from the adsorption materials 330a, 330b, and 330c when the adsorption materials 330a, 330b, and 330c are heated may also vary.

For example, the sensor 340 may detect a signal having a specific feature at a specific time point when the adsorption materials 330a, 330b, and 330c are heated to a specific temperature. Referring to FIG. 9B, for example, a first signal S1 output to have peaks A, B, and C may be detected for a first temperature profile, and a second signal S2 output to have peaks A, B, and C may be detected for a second temperature profile that is different from the first temperature profile. If the detection operations according to the first temperature profile and the second temperature profile are performed for the same two foods, the sequences and the features (the detection period of time (or speed)) of the peaks A, B, and C may be the same. If the detection operations according to the first temperature profile and the second temperature profile are performed for two different foods, the sequences and the features of the peaks A, B, and C may be quite different. If the detection operations according to the first temperature profile are performed for the two different foods, the sequences and the features of the peaks A, B, and C may be the same in the same way. Further, even when the detection operation according to the same first temperature profile is performed for two of the same foods, the period of time (or speed) for which the peaks A, B, and C are detected may be different according to the ripening degree.

The adsorption materials 330a, 330b, and 330c (i.e., information thereof) may be stored in a database in a memory within the interior of the refrigeration system 10 or a database of an external device (e.g., the server 20 or another electronic device). The detection sequences and features of signals according to various temperature profiles of the adsorption materials may also be stored in the database in advance. That is, the information related to the adsorption materials may be information that is already known during the detection operation through the gas detecting device 300. In comparison, the time point of extraction of the gasses measured by the sensor 340 may be identified in real time as the gases are actually desorbed after the heating of the adsorption materials 330a, 330b, and 330c. However, the time point of the extraction of the gases measured by the sensor 340 is dependent on the kinds (and/or combinations) of the adsorption materials 330a, 330b, and 330c, and the kind and the state of the foods in the storage container 223 may be determined through the information.

That is, the refrigeration system 10 according to an embodiment may determine the kind and the state of the foods at least on the basis of the kinds (and/or the combinations) of the adsorption materials 330a, 330b, and 330c and on the basis of the time point at which the gases desorbed from the adsorption materials 330a, 330b, and 330c are extracted.

The kind and the state of the foods may be distinguished according to the kinds and the concentrations of the detected gases. For reference, the state of the foods may include at least one of the state of the foods according to at least one of a lapsed time after the foods are stored, the state of the foods according to the freshness or the ripening degree of the foods, the cooked state of the foods, and the frozen state of the foods.

As an example of distinguishing the kind and the state of foods, it may be determined that the foods in the storage container are meat (beef) if ammonia is extracted through the signal acquired by the sensor 340, and it may be determined that the foods in the storage container are fruits and vegetables (apples) if ethylene is extracted through the signal acquired by the sensor 340. Of course, this is merely an example, and the actual kind and state of the foods will be determined through a more detailed and precise determination process, such as the concentration of the detected gas, detection of another gas, and the like.

FIG. 9C is a view illustrating a method of calculating the concentration of a detected gas.

The signal measured from the sensor 340 through the detection operation of FIG. 9B and the basic signal through the sampling operation of FIG. 9A may be compared. the concentration of the detected gas may be calculated by considering the difference D between the value of the signal measured from the sensor 340 and the basic signal.

Hereinafter, a method for identifying the kind and state of the foods in the refrigeration system 10 is described in detail.

The method for determining the kind and state of the foods of the refrigeration system 10 may be performed through calculation and processing operations of the processor 11.

According to an embodiment, the processor 11 may perform a plurality of operations included in the method for determining the kind and state of the foods according to an instruction stored in the memory 12 in advance.

According to an embodiment, the processor 11 may heat (e.g., control to heat) the gas detecting device 300 to heat the adsorption member 330. Further, the processor 11 may control to heat the adsorption member 330 by directly controlling the heating unit 333 included in the gas detecting device 300. For example, when a separate processor is included in the gas detecting device 300, the processor 11 may control the heating unit 333 by using the separate processor included in the gas detecting device 330. Alternatively, when the gas detecting device 300 does not include a separate processor, the processor 11 may control the heating unit to heat by directly controlling the heating unit.

According to an embodiment, the processor 11 may receive information (e.g., whether a gas was detected or the concentration of the detected gas) on the gases from the gas detecting device 300, and may identify a time point at which the gas was extracted through the received information.

According to an embodiment, the processor 11 may perform an operation of detecting at least one of the kind and the concentration of the desorbed gas by using information on the time point at which the gas received from the gas detecting device 300 is extracted, information related to a change of the temperature of the adsorption member 330, which was input in advance, and information on a predetermined configuration of at least one adsorption material included in the adsorption member.

According to an embodiment, the processor 11 may determine the kind and the state of the foods on the basis of at least one piece of information, among the kind and the concentration of the detected gas.

Hereinafter, in a description of a method for determining the kind and the state of the foods according to an embodiment, it is noted that the operations are performed through the processor 11. According to an embodiment, the processor 11 may determine the kind and the state of the foods at least partially on the basis of data provided from the memory 12 (or the database) in the refrigeration system 10 or data provided from the database of an external device (e.g., the server 20 or another electronic device) outside the refrigeration system 10, and at least partially on the basis of data on the kind and the state of the foods provided from the sensor 340 included in the gas detecting device 300.

Figure 10A:
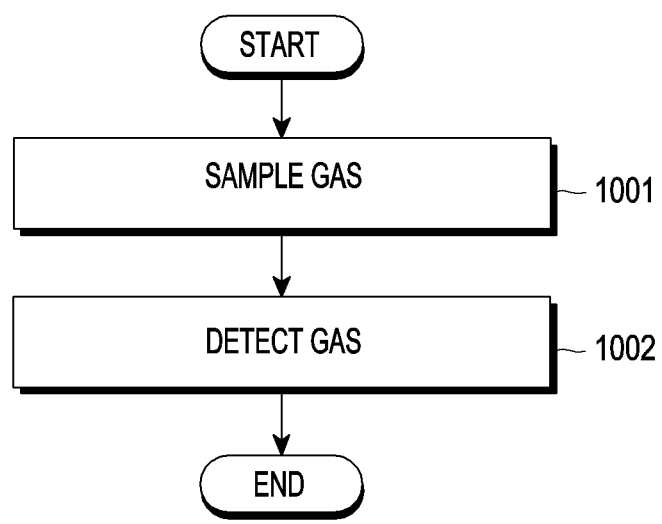
FIGS. 10A and 10B are flowcharts illustrating a method for determining the kind and the state of foods according to one or more embodiments.
Figure 10B:
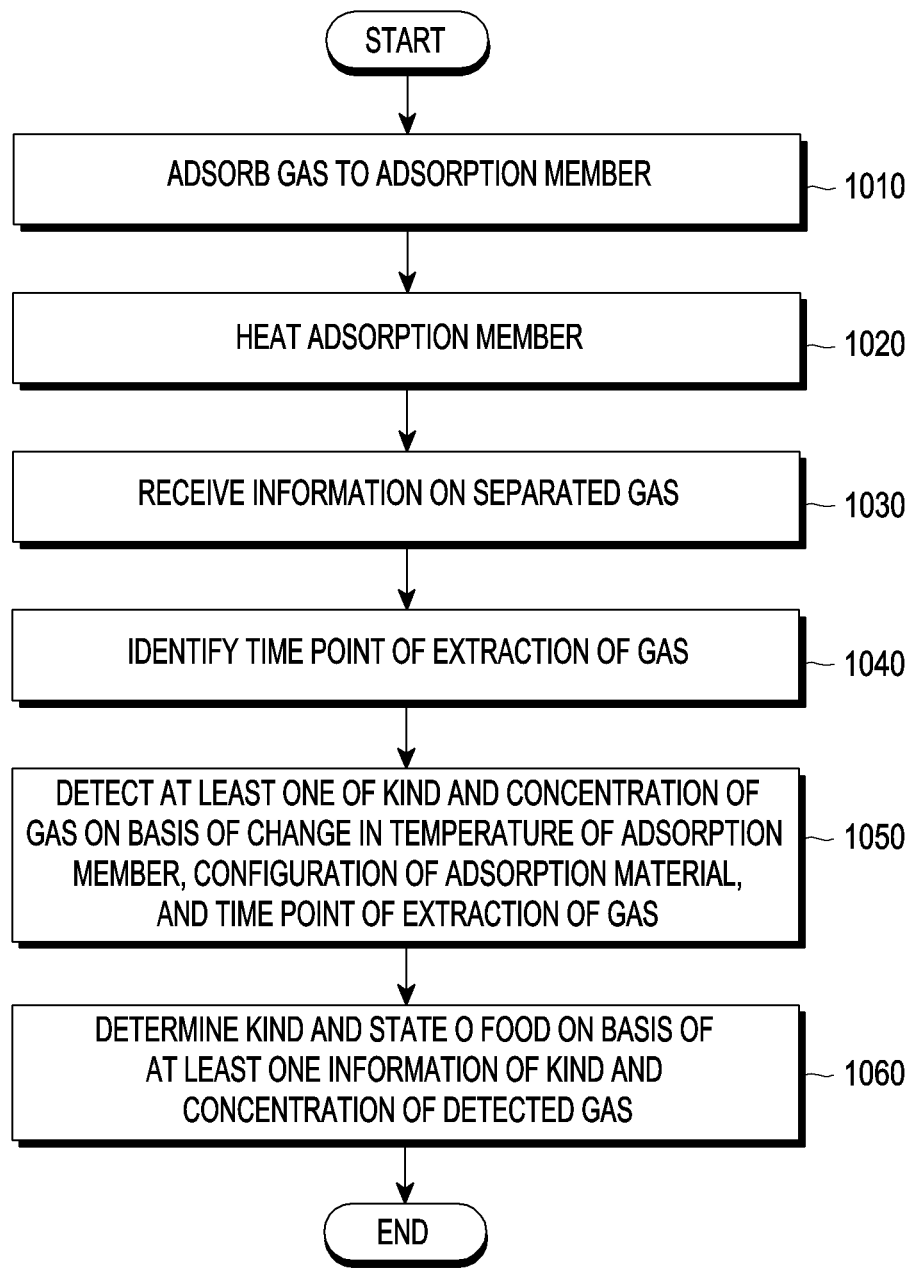

FIGS. 10A to 10B are flowcharts illustrating a method for determining the kind and the state of foods according to one or more embodiments. FIG. 10A illustrates a method for determining the kind and the state of the foods, and includes a sampling operation 1001 and a detection operation 1002. FIG. 10B illustrates a more detailed example of the method for determining the kind and the state of the foods of FIG. 10A.

The sampling operation 1001 and the detection operation 1002 may be performed for the purpose of determining the ripening degree and the decomposition degree of the foods in the storage container. According to various embodiments, the sampling operation 1001 and the detection operation 1002 may be performed according to a command of the user and/or a lapse of a period of time preset in the refrigeration system 10 or by a preset cycle.

The sampling operation 1001 may be an operation of extracting the gases contained in the air in the storage container 223, in which the food is stored, by using the gas detecting device 300. In general, the air in the storage container 223 may continuously circulate in the refrigerator 100 through the cooling system 150. A preliminary preparation for the following detection operation 1002 may be performed by extracting the gases contained in the air in the storage container 223 at any time point after the foods are stored through the sampling operation 1001.

According to an embodiment, the sampling operation 1001 is an operation of extracting gases, and may include an operation 1010 of adsorbing at least a portion of the gases to the adsorption member 330.

The detection operation 1002 may include a detection operation of identifying a time point of extraction of the sampled gases on the basis of a change of the temperature in the gas detecting device 300 while extracting the sampled gas from the gas detecting device 300 toward the outside of the gas detecting device 300 (e.g., the refrigeration system 150 or the storage container 223), and detecting the kind and the concentration of the gases on the basis of the configuration of the gas marking material included in the gas detecting device 300 and the time point of the extraction of the sampled gases. After the sampling operation 1001 is performed (e.g., after a predetermined period of time from the sampling operation 1001), the detection operation 1002 may be performed.

According to an embodiment, as the gas marking method, the above-described adsorption method may be used. That is, the adsorption materials 330a, 330b, and 330c may be utilized as the gas marking material.

According to an embodiment, the detection operation 1002 may include an operation 1020 of heating the adsorption member 330, an operation 1030 of receiving information on desorbed gases, and an operation 1040 of identifying a time point at which the gases desorbed from the adsorption member 330 are extracted on the basis of a change in the temperature of the adsorption member 330. Further, the detection operation 1002 may include an operation 1050 of detecting the kind and the concentration of the gases on the basis of a predetermined configuration of the at least one adsorption material 330a, 330b, and 330c included in the adsorption member 330 and a time point at which the gases desorbed from the adsorption member 330 are extracted.

Further, according to an embodiment, the detection operation 1002 may further include an operation 1060 of determining the kind and the state of the foods by comparing the kind and the concentration of the gases detected by the gas detecting device 300 and information included in the database in the interior of the refrigeration system 10 or in the server 20 outside the refrigeration system.

Figure 11:
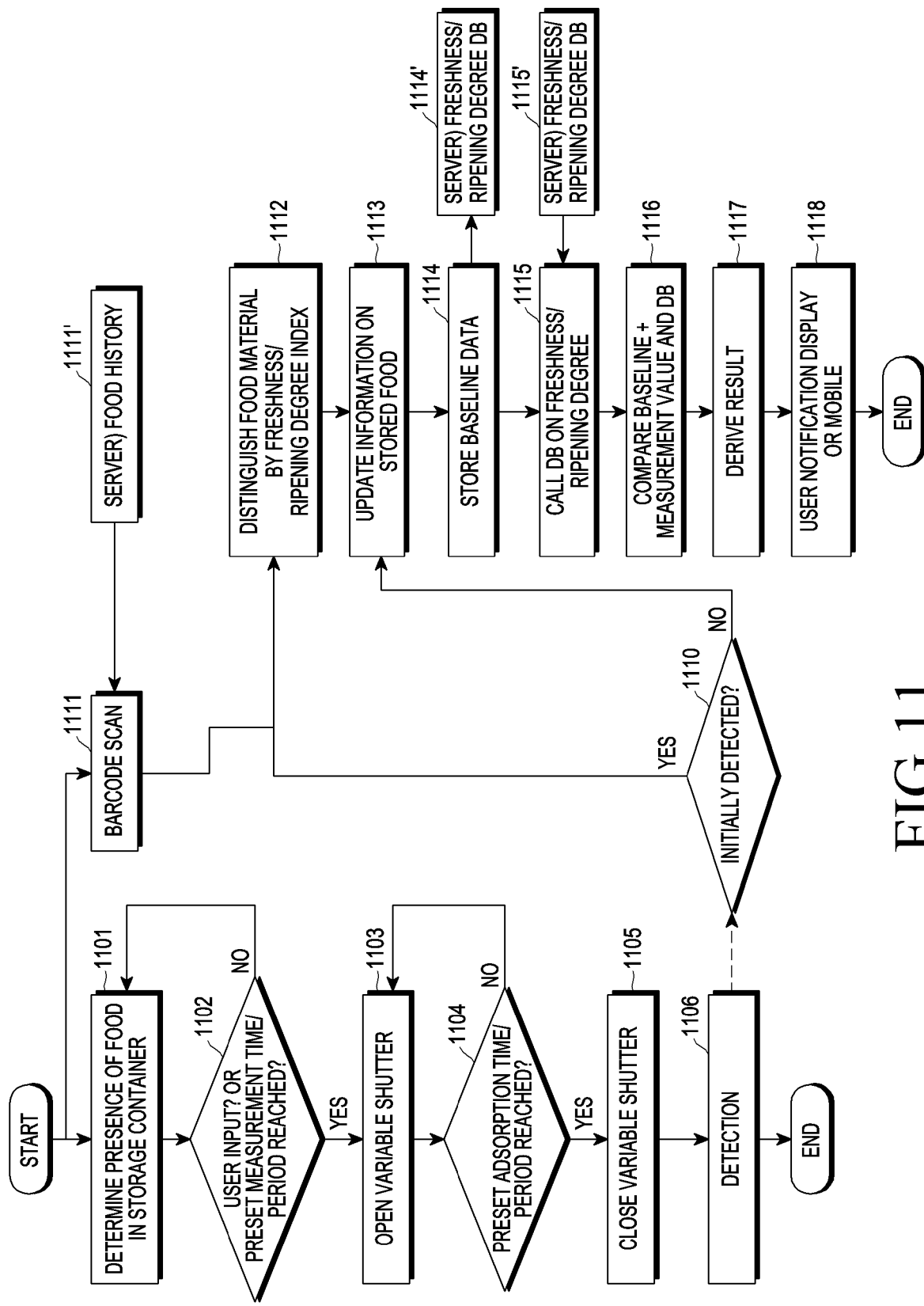
FIG. 11 is a flowchart illustrating a method for, by a refrigeration system, determining the kind and the state of foods according to another embodiment.
Figure 12:
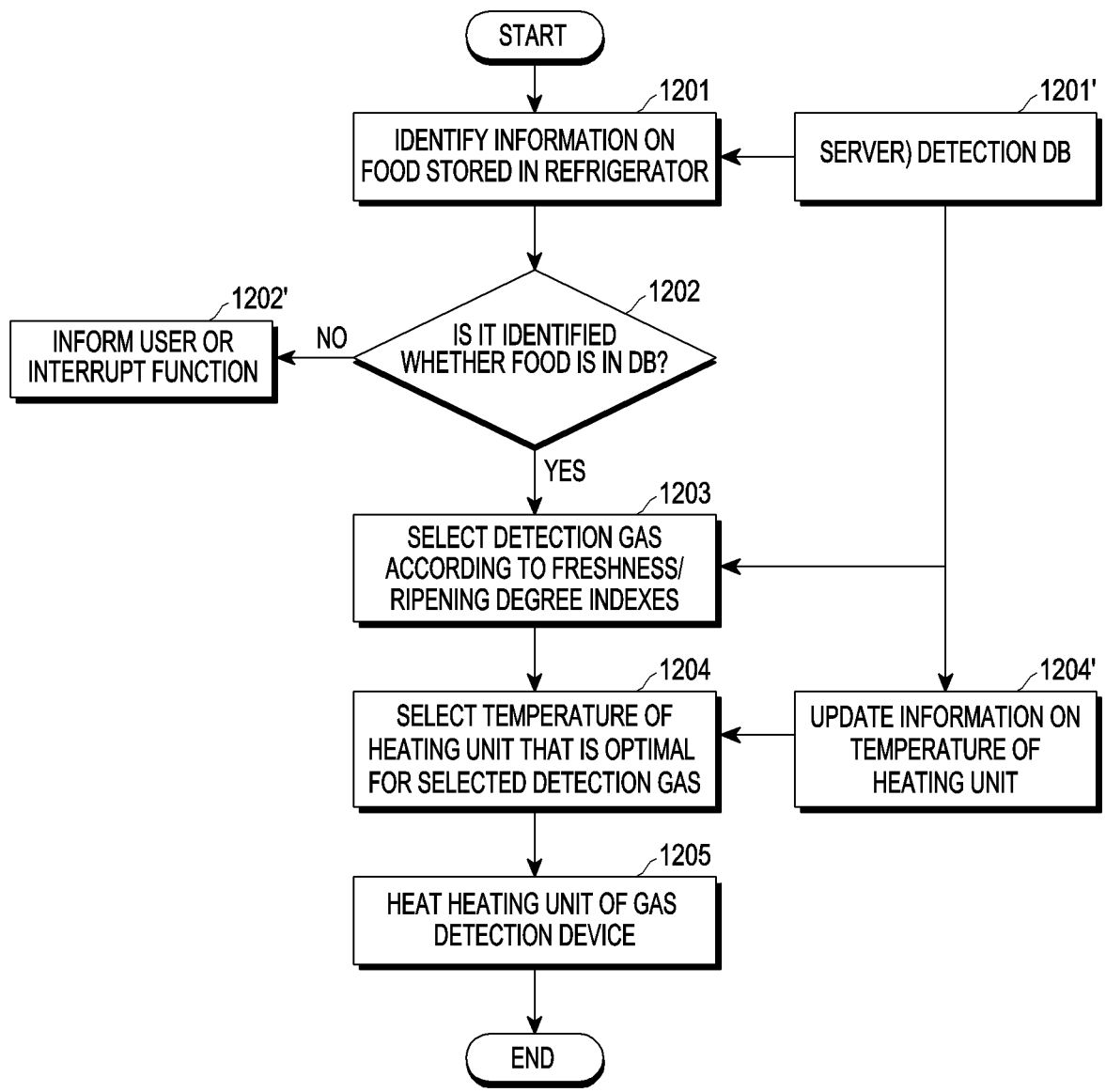
FIG. 12 is a view illustrating a detection operation in the flowchart of FIG. 11 in detail.

FIG. 11 is a flowchart illustrating a method for, by the refrigeration system 10, determining the kind and the state of foods according to another embodiment. FIG. 11 illustrates a method for, by the refrigeration system 10, determining the kind and the state of the foods, which is more specified than the flowchart of FIG. 10. FIG. 12 is a view illustrating a detection operation in the flowchart of FIG. 11 in detail.

Referring to FIG. 11, first, the processor 11 may perform an operation 1101 of determining whether foods are present in the storage container. According to an embodiment, the determination may be based on data provided from the memory 12 (or the database) in the refrigeration system 10 or a database provided from or of an external device (e.g., the server 20 or another electronic device) outside the refrigeration system 10. According to another embodiment, it may be determined whether foods are present in the storage container (operation 1101) through a weight measuring device provided in the refrigeration system 10.

If there are foods in the storage container, the processor 11 may determine (operation 1102) whether there is a user input or a preset measurement time/period has come.

Further, the processor 11 may perform an operation of sampling the gases contained in the air in the storage container 223 by opening the opening/closing unit 320 of the gas detecting device 300. In the sampling operation, the gases corresponding to the predetermined adsorption materials 330a, 330b, and 33c are adsorbed to the adsorption member 330 in the gas detecting device 300. FIG. 11 illustrates an operation 1103 of opening a variable shutter in which the variable shutter used as an operation of the opening/closing unit 320.

After the variable shutter is opened, the processor 11 may determine (operation 1104) whether the period of time, for which the gases are adsorbed to the adsorption materials 330a, 330b, and 330c in the gas detecting device 300, reaches a preset time/period.

Further, if it is determined that the period of time, for which the gases are adsorbed, reaches the preset time/period, the processor 11 may perform an operation of interrupting the opening/closing unit 320. FIG. 11 illustrates an operation 1105 of interrupting the variable shutter as an example of the opening/closing unit 320.

If the opening/closing unit 320 is interrupted such that the interior of the gas detecting device 300 is closed, the detection operation 1106 is performed, and the kind and the state of the foods in the refrigeration system 10 may be determined.

Referring to FIG. 12, a more detailed flowchart about the detection operation 1106 of FIG. 11 is illustrated.

In the detection 1106, according to an embodiment, the processor 11 may identify (operation 1201) information on foods stored in the refrigerator. The information on the foods stored in the refrigerator may be provided (operation 1201') from the database of the refrigeration system 10 or the external server 20. According to an embodiment, here, the information on the foods stored in the refrigerator may be information stored in advance through an act (e.g., a barcode input), by the user, of inputting information on the foods at a time point at which the foods in the refrigerator are stored by the user. According to various embodiments, here, the information on the foods stored in the refrigerator may not only be the information on the foods in the storage container 223 that is a detection target but also information on the foods in another storage container in the refrigerator.

The processor 11 may perform a procedure of selecting a detection gas according to freshness/ripening indexes when the foods stored in the database are actually stored in the storage container 223 for performing a gas detecting operation, as foods stored in the refrigerator. Unlike this, when the foods stored in the database are not stored in the storage container for performing the gas detecting operation (for example, another food is stored in the meat storage container or another food is detected from the storage container in a situation in which it is written that meat is stored in a barcode when the foods are stored, the processor 11 may inform the user of this or stop the function (a detection operation). Here, it may be identified whether the foods stored in the database are stored in the storage container by using an identification device (e.g., a camera) or a detection device (a separate sensor) separately provided in the refrigeration system 10.

The processor 11 may receive information on a detection gas according to the freshness/ripening indexes from the database of the refrigeration system 10 or the external server 20, and may select (operation 1203) what is the target gas to be detected according to the information on the foods stored in the refrigerator and the provided freshness/ripening indexes. Moreover, the processor 11 may select (operation 1204) an optimum temperature according to the actual extraction time point of the selected detection target gas. Then, the optimum temperature of the heating unit may be selected according to temperature information updated from the database of the refrigeration system 10 or the external server 20. Further, the gas detecting device may be heated (operation 1205) according to the optimum temperature of the heating unit.

In FIG. 12, after the operation 1205 of heating the gas detecting device heating unit, other operations may be omitted. For example, the operations after the operation 1020 of heating the adsorption member 330 in FIG. 10 may be performed after the heating unit heating operation 1205 of FIG. 12.

The above-described method for determining the kind and the state of the foods in the refrigeration system 10 may be repeated a plurality of times when the refrigeration system 10 is operated, and the information acquired through the repetition of the method may be updated in real time or continuously and more precise information may be provided to the user. The database in the interior of the refrigeration system 10 or the database of the server 20 (or an electronic device) outside the refrigeration system 10 may be utilized for the update. Further, the result derived according to the method and the updated information may be informed to the user to help selection of whether the user utilizes foods stored in the refrigeration system 10.

Referring back to FIG. 11, the processor 11 may determine (operation 1110) whether the detection operation was performed initially after the detection operation is performed. For example, when the detection operation is the detection operation that was initially performed after meat (beef) is stored in the storage container, the food materials are distinguished (operation 1112) on the basis of the freshness/ripening indexes secured according to the detection result, and the information on a new stored food may be updated (operation 1113) in the database of the refrigeration system 10 or the database of the external server 20. If the detection operation is not the initial detection operation, the existing information on the stored foods may be updated (operation 1113) in the database of the refrigeration system 10 or the external server 20.

Moreover, the processor 11 may store information (baseline data) on the surrounding environment (or the basic environment in the storage container) of the adsorption member 330 acquired through the sensor 340. As described above, when the operation for detecting a target gas by the gas detecting device 300 is not an initial one, that is, the detection operation is performed at least once before, there may be present a residual target gas or other gases around the adsorption member 330, and this may influence the precise determination of the current state of the foods in the refrigerator 100. Accordingly, in order to minimize the influence, the baseline data acquired by using the sensor 340 may be stored and utilized. The baseline data may be stored (operation 1114') in the database, in which the data of the refrigeration system 10 or the external server 20, which are related to the freshness and the ripening degree of the foods is provided. The database, in which the data related to the freshness and the ripening degree of the foods is provided, may include information on the configurations of the adsorption materials 330a, 330b, and 330c, information on the temperature profile corresponding to the configurations of the adsorption materials 330a, 330b, and 330c, and baseline data acquired by using the sensor 340.

The processor 11 may compare (calculate) (operation 1116) information on the baseline data and the gas extraction time point detected from the sensor 340 after recent data on the configurations of the adsorption materials 330a, 330b, and 330c are secured (operation 1115) from the database, in which the data related to the freshness and the ripening degree of the foods and the recent data are included, and may derive (operation 1117) a detection result.

Further, the processor 11 may help the user to select processing of the foods according to the detection result by informing the user of the detection result.

Meanwhile, at a time point at which the foods are stored in the refrigeration system 10, the user may directly input (operation 1111) the information on the foods to the refrigeration system 10. As an example of an input device, a device for recognizing a barcode of a food may be provided, and if the user inputs the barcode of the food, the data of the refrigeration system 10 or the external server 20, which are related to the history of the food, are provided (operation 1111') and the foods in the refrigeration system 10 may be distinguished according to the freshness and ripening indexes. The device for recognizing the barcode of the foods may be provided in the refrigeration system 10, or may be provided separately from the refrigeration system 10 (e.g., a camera module of a portable terminal of the user).

Figure 13:
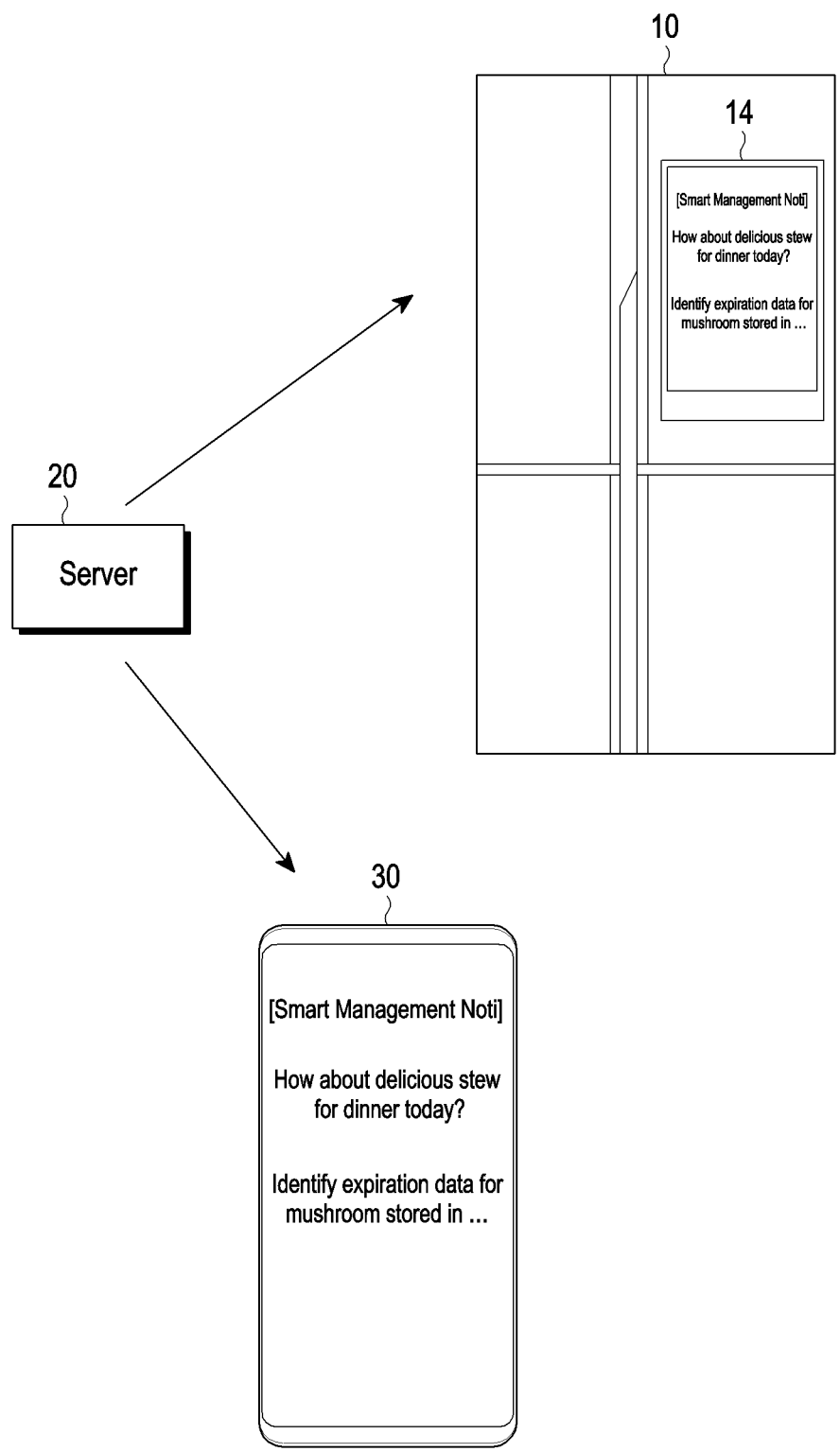
FIG. 13 is a view illustrating a method for providing information to a user according to the determined kind and the determined state of foods according to an embodiment.

FIG. 13 is a view illustrating a method for providing information to a user according to the determined kind and the determined state of foods according to an embodiment.

According to various embodiments, the information on the kind and the state of the food may be provided to the user through the communication module 16 provided in the refrigeration system 10 or the server 20 provided outside the refrigeration system. FIG. 13 illustrates a method for providing information on the kinds and the states of foods to a user through the server 20.

Referring to FIG. 13, as an embodiment, information on the kinds and the states of the foods may be provided to the user through a display device 14 provided in the refrigeration system 10. For example, when meat (e.g., steak) is stored in a certain container in the refrigeration system 10, the refrigeration system 10 performs a gas sampling and detection operation for the meat, and may provide the result to the user through a display unit (e.g., display) of the refrigeration system 10.

As another embodiment, the information on the kinds and the states of the foods may be provided to the user through a user terminal 30 registered in the server 20 or with access to the server 20 (e.g., via a web page and authentication procedure). For example, when meat (e.g., steak) is stored in a certain container in the refrigeration system 10, the refrigeration system 10 performs a gas sampling and detection operation for the meat, and may provide the result to the user through a display unit of the user terminal 30.

Figure 14:
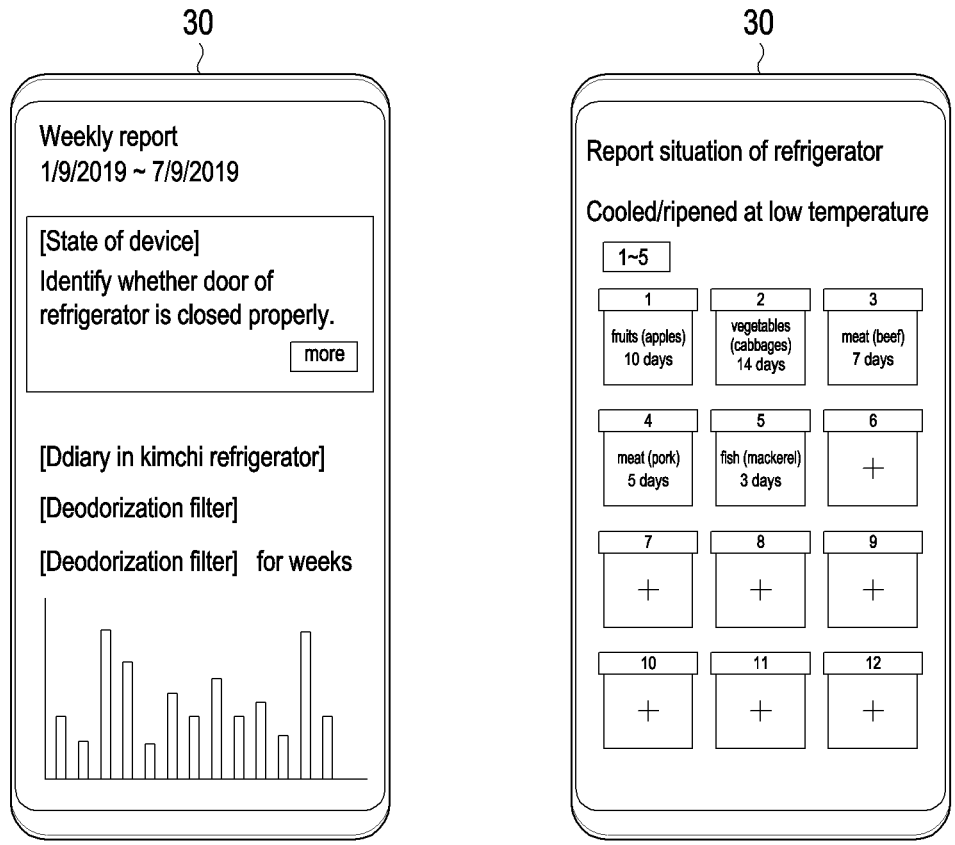
FIG. 14 is a view illustrating various embodiments of refrigeration system related information provided to a user.

FIG. 14 is a view illustrating various embodiments of refrigeration system related information provided to the user.

Referring to FIG. 14, the refrigeration system related information provided to the user may include state information of devices of the refrigerator, information on a specific storage (e.g., a Kimchi refrigerator) in the refrigerator, and information on other functions (deodorization). Further, according to an embodiment, the numbers of openings of the doors of the refrigerator or statistical information according to use of the refrigeration system may be provided.

Further, separately from the above-described embodiment, as the refrigeration system related information provided to the user, food storage information on a plurality of storage containers (e.g., one to twelve storage containers) included in the refrigeration system may be provided.

According to the above-described method for determining the kind and the state of the foods, the ripening degrees and the decomposition degrees of the foods in the storage containers may be provided to the user. For example, FIG. 14 illustrates that fruits (apples) have been stored in compartment 1 of the storage container for more than 10 days, that vegetable (cabbages) have been stored in compartment 2 of the storage container for more than 14 days, and that meat (beef) has been stored in compartment 3 of the storage container for more than 7 days. Further, FIG. 14 illustrates that meat (pork) has been stored in compartment 4 of the storage container for more than 5 days, and that fish (mackerel) has been stored in compartment 2 of the storage container for more than 3 days.

In this way, according to the refrigeration system and the method for identifying the state of an article in accordance with one or more embodiments, a low-concentration gas detecting device that can be installed in a refrigeration system may be provided.

Further, according to the refrigeration system and the method for identifying the state of an article in accordance with one or more embodiments, a low concentration gas detecting device that can select various gases generated from foods and analyze the selected gases may be provided.

Additionally, according to the refrigeration system and the method for identifying the state of an article in accordance with one or more embodiments, a precise state of foods can be determined by detecting the decomposition degree of the foods stored in a refrigeration system.

Moreover, according to the refrigeration system and the method for identifying the state of an article in accordance with one or more embodiments, the kind and the state of foods included in one storage container, as well as the kinds and states of the foods included in a plurality of storage containers, can be determined.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "at least one of A and B," "at least one of A or B," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively," as "coupled with," or "connected with," that element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments of the disclosure may be implemented by software (e.g., a program) including one or more instructions stored in a storage medium (e.g., an internal memory or an external memory) that may be read by a machine (e.g., the refrigeration system 10). For example, a processor (e.g., the processor 11) of the machine (e.g., the electronic device 10) may invoke at least one of the one or more instructions stored in the storage medium, and execute it. This allows the machine to be operated to perform at least one function according to the invoked at least one instruction. The one or more instructions may include a code generated by a compiler or a code executable by an interpreter. The machine-readable storage medium may be provided in the form of a non-transitory storage medium, which is a tangible device, and does not include a signal (e.g., an electromagnetic wave), and does not differentiate between where data is semi-permanently stored in the storage medium and where the data is temporarily stored in the storage medium.

A method according to various embodiments may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more components of the above-described components or operations may be omitted, or one or more other components or operations may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to various embodiments, there may be provided an electronic device usable for storing foods, the electronic device may include at least one storage container in which foods are stored, an adsorption member configured to adsorb at least a portion of gas contained in air in the at least one storage container, a heating unit configured to heat the adsorption member, and a gas detecting device including a sensor configured to sense gas desorbed when the adsorption member is heated, and at least one processor, wherein in order to detect at least one of the kind and the concentration of the gas generated from the foods in the at least one storage container, the processor is configured to control the heater to heat the adsorption member, receive, from the gas detecting device, information on the gas desorbed from the adsorption member as the adsorption member is heated, identify a time point at which the gas is extracted on the basis of the information on the gas received from the gas detecting device, detect at least one of the kind and the concentration of the desorbed gas on the basis of at least one of a temperature change of the adsorption member according to the heating of the adsorption member, a predetermined configuration of at least one adsorption material contained in the adsorption member, and a time point at which the desorbed gas is extracted from the adsorption member, and determine the kind and the state of the foods on the basis of at least one information of the kind and the concentration of the detected gas.

According to various embodiments, the state of the foods may include at least one of the state of the foods according to a lapse time after the foods are stored, the state of the foods according to the freshness or the ripening degree of the foods, the cooked state of the foods, and the frozen state of the foods.

According to various embodiments, the gas detecting device may be installed in a specific storage container, among the at least one storage container in which the foods are stored, and the specific storage container may be used as a dedicated container for determining the kind and the state of the foods.

According to various embodiments, the gas detecting device further may include a housing, an opening/closing unit disposed on at least one side of the housing, and a sensor for sensing the gas desorbed from the adsorption member, and the adsorption member may be accommodated in the interior of the housing, and adsorb the gas contained in the air when the opening/closing unit is opened.

According to various embodiments, the housing of the gas detecting device may form an at least temporarily closed space according to an operation of the opening/closing unit.

According to various embodiments, the opening/closing unit may cause the air in the storage container to flow into the interior of the housing through diffusion.

According to various embodiments, the gas detecting device may further include a scrubber for collecting the gas generated from the foods.

According to various embodiments, the electronic device may further include a filter unit for extracting a target gas by filtering the material desorbed from the adsorption member.

According to various embodiments, the filter unit may include a porous material including a metal organic framework (MOF).

According to various embodiments, the metallic material in the MOF may include at least one material of Pt, Zn Cu, Be, Fe, Ni, W, Co, Mn, Mo, Cr, Mg, V, Li, Ca, and Na.

According to various embodiments, the MOF may include a material having at least one functional group of —COOCu, —COOAg, —HSO4, —COOLi, —S3H, —OP(=O)OH2, —P(=O)(OH)2, —OH, and —COOH.

According to various embodiments, the processor may be configured to control the temperature of the storage container according to the determined kind and the determined state of the foods.

According to various embodiments, a method for determining the kind and the state of foods in an electronic device may include a sampling operation of extracting gas contained in air in a storage container, in which foods are stored, by using a gas detecting device, and a detection operation of identifying an extraction time point of the sampled gas while extracting the sampled gas toward the outside of the gas detecting device, and detecting the kind and the concentration of the gas on the basis of a temperature change of the gas detecting device, a configuration of a gas marking material contained in the gas detecting device, and an extraction time point of the sampled gas.

According to various embodiments, the sampling operation may include adsorbing at least a portion of the gas contained in the air in the storage container, in which the foods are stored, to the adsorption member.

According to various embodiments, the detection operation may include heating the adsorption member, receiving information on gas desorbed from the adsorption member, from the gas detecting device, identifying a time point at which the gas is extracted on the basis of the information on the gas received from the gas detecting device, and detecting at least one of the kind and the concentration of the adsorbed and desorbed gas on the basis of at least one of a temperature change of the adsorption member according to the heating of the adsorption member, a predetermined configuration of at least one adsorption material contained in the adsorption member, and a time point at which the adsorbed and desorbed gas is extracted from the adsorption member.

According to various embodiments, the detection operation may further include determining the kind and the state of the foods by comparing at least one of the kind and the concentration of the gas detected by the gas detecting device and information contained in a database in the electronic device or a server outside the electronic device.

According to various embodiments, the sampling operation and the detection operation may be performed according to at least one of a command of a user or a preset period.

According to various embodiments, the processor may be configured to control the temperature of the storage container according to the determined kind and the determined state of the foods.

According to various embodiments, the processor may be configured to control the humidity of the storage container according to the determined kind and the determined state of the foods.

According to various embodiments, the state of the foods may include at least one of the state of the foods according to a lapse time after the foods are stored, the state of the foods according to the freshness or the ripening degree of the foods, the cooked state of the foods, and the frozen state of the foods.

While the disclosure has been shown and described with reference to certain embodiments thereof, it will be understood by those skilled in the art that various changes in form and details may be made therein without departing from the spirit and scope of the disclosure as defined by the appended claims.

What is claimed is:

1. An electronic device usable for storing foods, the electronic device comprising:
    a storage container;
    a gas detecting device comprising:
        an adsorption member configured to adsorb at least a portion of gas contained in air in the storage container;
        a heater configured to heat the adsorption member; and
        a sensor configured to sense gas desorbed based on the adsorption member being heated; and
    at least one processor configured to detect at least one from among a kind of the desorbed gas and a concentration of the desorbed gas generated from food stored in the storage container, the at least one processor configured to:
        control the heater to heat the adsorption member;
        receive, from the gas detecting device, information on the desorbed gas based on the adsorption member being heated;
        identify a time point at which the desorbed gas is extracted from the adsorption member based on the received information on the desorbed gas;
        detect the at least one from among the kind of the desorbed gas and the concentration of the desorbed gas based on a temperature change of the adsorption member according to the heating of the adsorption member, a predetermined component of the adsorption member containing at least one adsorption material, and the time point at which the desorbed gas is extracted from the adsorption member; and
        determine a kind of the food and a state of the food based on the detected at least one from among the kind of the desorbed gas and the concentration of the desorbed gas.

2. The electronic device of claim 1, wherein the state of the food comprises at least one of the state of the food according to a lapsed time after the food is stored, the state of the food according to a freshness or a ripening degree of the food, a cooked state of the food, and a frozen state of the food.

3. The electronic device of claim 1, wherein the gas detecting device is inside the storage container, and the storage container is a dedicated container for determining the kind of the food and the state of the food.

4. The electronic device of claim 1, wherein the gas detecting device further comprises:
    a housing;
    an opening/closing unit disposed on at least one side of the housing,
    wherein the adsorption member is accommodated in an interior of the housing, and adsorbs the gas contained in the air when the opening/closing unit is opened.

5. The electronic device of claim 4, wherein the housing of the gas detecting device forms an at least temporarily closed space according to an operation of the opening/closing unit.

6. The electronic device of claim 4, wherein the opening/closing unit is configured to allow the air in the storage container to flow into the interior of the housing through diffusion.

7. The electronic device of claim 4, wherein the gas detecting device further comprises a scrubber configured to collect the gas generated from the food.

8. The electronic device of claim 4, further comprising:
    a filter configured to extract a target gas by filtering material desorbed from the adsorption member.

9. The electronic device of claim 8, wherein the filter comprises a porous material comprising a metal organic framework (MOF).

10. The electronic device of claim 9, wherein a metallic material in the MOF comprises at least one of Pt, Zn Cu, Be, Fe, Ni, W, Co, Mn, Mo, Cr, Mg, V, Li, Ca, and Na.

11. The electronic device of claim 9, wherein the MOF comprises a material having at least one functional group of —COOCu, —COOAg, —HSO4, —COOLi, —SO3H, —OP(=O)OH2, —P(=O)(OH)2, —OH, and —COOH.

12. The electronic device of claim 1, wherein the at least one processor is further configured to control a temperature of the storage container according to the determined kind of the food and the determined state of the food.

13. A method for determining at least one of a kind and a state of foods in an electronic device, the method comprising:
    sampling, using a gas detecting device, gas contained in air in a storage container configured to store food;
    controlling a heater to heat an adsorption member of the gas detecting device;
    sensing gas desorbed based on the adsorption member being heated;
    receiving, from the gas detecting device, information on the desorbed gas based on the adsorption member being heated;

identifying an extraction time point at which the desorbed gas is extracted from the adsorption member based on the received information on the desorbed gas;

detecting at least one from among a kind of the desorbed gas and a concentration of the desorbed gas based on a temperature change of the adsorption member according to the heating of the adsorption member, a predetermined component of the adsorption member containing at least one adsorption material, and the extraction time point at which the desorbed gas is extracted from the adsorption member; and determining a kind of the food and a state of the food based on the detected at least one from among the kind of the desorbed gas and the concentration of the desorbed gas.

14. The method of claim 13, wherein the detecting further comprises:

determining the kind of the food and the state of the food by comparing the at least one from among the kind of the desorbed gas and the concentration of the desorbed gas detected by the gas detecting device and information contained in a database stored in the electronic device or a server outside the electronic device.

15. The method of claim 13, wherein the sampling and the detecting are performed according to a command of a user or a preset period.

16. The method of claim 13, further comprising, based on the determined kind of the food and the state of the food, controlling a temperature or a humidity of the storage container.

17. The method of claim 13, wherein the state of the food comprises at least one of the state of the food according to a lapsed time after the food is stored, the state of the food according to a freshness or a ripening degree of the food, a cooked state of the food, and a frozen state of the food.

18. An electronic device comprising:
a memory storing instructions; and
at least one processor configured to execute the instructions to:

control a heater to heat an adsorption member for adsorbing at least a portion of gas contained in air in a storage container;

receive information on gas desorbed based on the adsorption member being heated;

identify a time point at which the desorbed gas is extracted from the adsorption member based on the received information on the desorbed gas;

detect at least one from among a kind of the desorbed gas and a concentration of the desorbed gas based on a temperature change of the adsorption member according to the heating of the adsorption member, a predetermined component of the adsorption member containing at least one adsorption material, and the time point at which the desorbed gas is extracted from the adsorption member; and determine a kind of food and a state of the food stored in the storage container based on the detected at least one from among the kind of the desorbed gas and the concentration of the desorbed gas.

* * * * *